United States Patent
Ben Yehuda

(10) Patent No.: US 10,212,956 B2
(45) Date of Patent: Feb. 26, 2019

(54) COMPOSITIONS AND METHODS OF TREATING EDIBLE MATTER AND SUBSTRATES THEREFOR

(71) Applicant: PIMI AGRO CLEANTECH LTD., Hutzot Alonim (IL)

(72) Inventor: Nimrod Ben Yehuda, Kiryat Tivon (IL)

(73) Assignee: PIMI AGRO CLEANTECH LTD., Alonim (IL)

( * ) Notice: Subject to any disclaimer, the term of this patent is extended or adjusted under 35 U.S.C. 154(b) by 0 days.

(21) Appl. No.: 15/361,432

(22) Filed: Nov. 27, 2016

(65) Prior Publication Data

US 2017/0295830 A1    Oct. 19, 2017

Related U.S. Application Data

(63) Continuation of application No. 13/830,982, filed on Mar. 14, 2013, now abandoned, which is a continuation-in-part of application No. PCT/US2011/051663, filed on Sep. 14, 2011.

(60) Provisional application No. 61/382,921, filed on Sep. 14, 2010.

(51) Int. Cl.

| | | |
|---|---|---|
| *A23L 3/3598* | (2006.01) | |
| *A23L 3/26* | (2006.01) | |
| *A23L 3/3481* | (2006.01) | |
| *A23L 3/358* | (2006.01) | |
| *A23L 19/12* | (2016.01) | |
| *A23L 19/10* | (2016.01) | |
| *A23B 4/20* | (2006.01) | |
| *A23B 4/24* | (2006.01) | |
| *A23B 5/14* | (2006.01) | |
| *A23B 5/18* | (2006.01) | |
| *A23B 7/154* | (2006.01) | |
| *A23B 7/157* | (2006.01) | |
| *A23B 9/26* | (2006.01) | |
| *A23B 9/30* | (2006.01) | |
| *A23C 3/08* | (2006.01) | |
| *A01N 37/02* | (2006.01) | |
| *A01N 37/16* | (2006.01) | |
| *A01N 25/22* | (2006.01) | |
| *A23L 3/3508* | (2006.01) | |

(52) U.S. Cl.
CPC ............ *A23L 3/3508* (2013.01); *A01N 25/22* (2013.01); *A01N 37/02* (2013.01); *A01N 37/16* (2013.01); *A23B 4/20* (2013.01); *A23B 4/24* (2013.01); *A23B 5/14* (2013.01); *A23B 5/18* (2013.01); *A23B 7/154* (2013.01); *A23B 7/157* (2013.01); *A23B 9/26* (2013.01); *A23B 9/30* (2013.01); *A23C 3/08* (2013.01); *A23L 3/26* (2013.01); *A23L 3/3481* (2013.01); *A23L 3/358* (2013.01); *A23L 19/105* (2016.08); *A23L 19/12* (2016.08)

(58) Field of Classification Search
CPC ........ A01N 37/36; A01N 37/02; A01N 37/16; A01N 59/06; A01N 59/20; A01N 59/26; A01N 59/00; A01N 25/22; A01N 59/16; A23B 5/14; A23B 5/184; A23B 7/154; A23B 7/157; A23B 9/26; A23B 9/30; A23C 3/08; A23L 3/26; A23L 3/3481; A23L 3/3508; A23L 3/358; A23L 19/105; A23L 19/12

See application file for complete search history.

(56) References Cited

U.S. PATENT DOCUMENTS

| | | |
|---|---|---|
| 4,550,026 A * | 10/1985 | Ando .................. A21D 15/00 422/29 |
| 5,589,507 A | 12/1996 | Hall et al. |
| 6,210,678 B1 | 4/2001 | Richards |
| 6,211,637 B1 | 4/2001 | Studer |
| 6,284,793 B1 | 9/2001 | Fuchs et al. |
| 2002/0128312 A1* | 9/2002 | Hei ...................... A01N 37/16 514/529 |
| 2003/0047087 A1 | 3/2003 | Phebus et al. |
| 2004/0035537 A1 | 2/2004 | Delmas et al. |
| 2004/0143133 A1 | 7/2004 | Smith et al. |
| 2005/0118940 A1* | 6/2005 | Hilgren ................. A01N 37/16 452/173 |
| 2009/0221704 A1 | 9/2009 | Akesela et al. |
| 2009/0312279 A1 | 12/2009 | Mookerjee et al. |
| 2010/0119669 A1 | 5/2010 | Ben Yehuda et al. |

FOREIGN PATENT DOCUMENTS

| | | |
|---|---|---|
| WO | 94/20424 A1 | 9/1994 |
| WO | 95/24388 A1 | 9/1995 |
| WO | 01/70030 A2 | 9/2001 |

OTHER PUBLICATIONS

International Search Report for PCT/US2011/051633, dated Apr. 27, 2012.
Written Opinion of the International Search Authority for PCT/US2011/051633, dated Apr. 27, 2012.

\* cited by examiner

*Primary Examiner* — Sarah Pihonak
(74) *Attorney, Agent, or Firm* — Daniel Feigelson; Fourth Dimension IP

(57) ABSTRACT

There are provided methods of treating edible matter comprising applying a composition comprising performic acid to the edible matter or a substrate therefor. Other embodiments are also disclosed.

69 Claims, No Drawings

COMPOSITIONS AND METHODS OF TREATING EDIBLE MATTER AND SUBSTRATES THEREFOR

RELATED APPLICATIONS

This application is a continuation of U.S. Ser. No. 13/830, 982, entitled "COMPOSITIONS AND METHODS OF TREATING EDIBLE MATTER AND SUBSTRATES THEREFOR" and filed Mar. 14, 2013 as a continuation-in-part of PCT/US2011/051663, entitled "COMPOSITIONS AND METHODS OF TREATING EDIBLE MATTER AND SUBSTRATES THEREFOR", filed Sep. 14, 2011, which claims the benefit of U.S. Provisional Application No. 61/382,921, entitled "COMPOSITIONS AND METHODS OF TREATING EDIBLE MATTER AND SUBSTRATES THEREFOR", filed on Sep. 14, 2010. The contents of the aforementioned applications are incorporated herein by reference in their entireties.

FIELD

The present invention is generally directed to compositions and methods that can be used to, among other things, protect foodstuffs and agricultural products from decay.

BACKGROUND

The qualitative and/or quantitative loss of edible matter such as grains, fruits, vegetables and meat during storage, for example, from undesirable microorganisms, or from the natural processes of the edible matter itself, for instance natural decay processes or unwanted sprouting, is a known problem. Indeed, agricultural losses of as much as 30%-40% due to such processes are not out of the norm. Although methods for reducing or preventing such detrimental processes are known, the known methods often add toxic substances, sometimes in large amounts, to the edible matter or to the environment. In fact, certain agents used in agriculture, such as some pesticides, are being phased out by regulations in countries around the globe because of concerns about their impact on the environment.

BRIEF DESCRIPTION

As will be explained in greater detail below, there are provided in accordance with various embodiments of the invention methods and compositions for protecting edible matter from decay and reducing losses thereof. The methods in accordance with some embodiments of the invention comprise contacting the edible matter, or a substrate therefor, with performic acid. In general, the performic acid is provided as part of a composition containing performic acid, and while some such compositions per se are known, there are provided in accordance with embodiments of the invention novel such compositions, as well as processes for making such novel compositions.

DESCRIPTION OF VARIOUS EMBODIMENTS

There is provided, in accordance with an embodiment of the invention, a method, comprising contacting edible matter or a substrate therefor with a composition comprising performic acid. In accordance with another embodiment of the invention, there is provided a method for protecting edible matter from decay, comprising contacting edible matter or a substrate therefor with a composition comprising performic acid for a time and in an amount and/or at a concentration sufficient to protect said edible matter from said decay. In accordance with another embodiment of the invention, there is provided a method for killing weeds or foliage, comprising contacting an area in which weeds grow with a composition comprising performic acid or a performic acid source and an oxidizer for a time and in an amount and/or at a concentration sufficient to kill said weeds or foliage or to prevent their growth.

In some embodiments, the composition is such that at a concentration of 20 ppm performic acid and a contact time of one minute at room temperature, the composition achieves a 10,000-fold (4 log) reduction in the colony forming units (cfu) of a pathogen grown on a designed growth medium, wherein the pathogen is at least one of the pathogens in the group consisting of *Escherichia coli* (ATCC 8739), *Staphylococcus aureus* (ATCC 6538), *Pseudomonas aeruginosa* (ATCC 9027), *Enterococcus hirae* (ATCC 10541), *Candida albicans* (ATCC 10231), *Aspergillus niger* (ATCC 16404) and *Penecillium* w.t. (wild type). In some embodiments, the composition is such that at a concentration of 20 ppm performic acid and a contact time of one minute at room temperature, the composition achieves a 100,000-fold (5 log) reduction in the cfu of a pathogen grown on a designed growth medium, wherein the pathogen is at least one of the pathogens in the group consisting of *Escherichia coli* (ATCC 8739), *Staphylococcus aureus* (ATCC 6538), *Pseudomonas aeruginosa* (ATCC 9027), *Enterococcus hirae* (ATCC 10541). In some embodiments, with a one-minute contact time the composition meets or exceeds at least one of the following Standards: BS EN 1276:1997, BS EN 1650:1998, BS EN 13697:2001, BS EN 1276:2009. In some embodiments, the composition exceeds at least one of Standard BS EN 1276:1997 or Standard BS EN 1276:2009. In some embodiments, the composition possesses bactericidal activity within one minute at 20° C. under dirty conditions of 3.0 g/l bovine albumin for at least one of the reference strains *E. coli* (ATCC 8739), *Staphylococcus aureus* (ATCC 6538), *Pseudomonas aeruginosa* (ATCC 9027), *Enterococcus hirae* (ATCC 10541) and *Listeria monocytogenes* (ATCC 19115). In some embodiments, the composition possesses bactericidal activity within one minute at 20° C. under dirty conditions of 3.0 g/l bovine albumin for the reference strains *E. coli* (ATCC 8739), *Staphylococcus aureus* (ATCC 6538), *Pseudomonas aeruginosa* (ATCC 9027), and *Enterococcus hirae* (ATCC 10541). In some embodiments, the composition exceeds at least one of Standard BS EN 1650:1998 and Standard BS EN 13697:2001. In some embodiments, the composition possesses fungicidal activity within one minute at 20° C. under dirty conditions of 3.0 g/l bovine albumin for at least one of the reference strains *Candida albicans, Aspergillus brasiliensis (Aspergillus niger),* and *Penecilium* w.t. In some embodiments, the composition possesses fungicidal activity within one minute at 20° C. under dirty conditions of 3.0 g/l bovine albumin for the reference strains *Candida albicans, Aspergillus brasiliensis (Aspergillus niger),* and *Penecilium* w.t. In some embodiments, the composition exceeds Standard BS EN 13697:2001. In some embodiments, the composition is a composition according to any one of original claims 61 to 106 or a composition in accordance with embodiment of the invention.

In some embodiments, the edible matter is selected from the group consisting of fruits, vegetables, grains, sprouts, nuts, seeds, meats, meat products, milk, milk products, fish, poultry, eggs, and mixtures thereof. In some embodiments, the edible matter is selected from the group consisting of apple, avocado, citrus—mandarin, citrus—orange, citrus—mineola, citrus—grapefruit, citrus—lemon, date, kiwi, lychee, mango, peach, pear, persimmon, pomegranate, pepper, asparagus, banana, broccoli, cabbage, carrot, cauliflower, celery, corn, kohlrabi, cucumber, eggplant, garlic, lettuce, onion, peanut, potato, strawberry, sweet pepper, sweet potato, tomato, watermelon, and grape. In some embodiments, the edible matter is not fully cooked, e.g. the edible matter is uncooked or only partially cooked.

In some embodiments, by said contacting said composition kills at least one of a strain of bacteria, a fungus, a yeast, a virus, and an algae, a mold, protozoa, an amoeba, and spore-propagating microorganisms. In some embodiments, said bacteria is selected from the group consisting of gram-positive bacteria. In some embodiments, said gram-positive bacteria are selected from the group consisting of *Staphylococcus, Streptococcus, Enterococcus, Bacillus, Corynebacterium, Nocardia, Clostridium, Actinobacteria* and *Listeria*. In some embodiments, said bacteria is selected from the group consisting of gram-negative bacteria. In some embodiments, said gram-negative bacteria are selected from the group consisting of *Escherichia, Salmonella, Shigella, Enterobacteriaceae, Pseudomonas, Moraxella, Helicobacter, Stenotrophomonas, Bdellovibrio*, acetic acid bacteria, *Legionella*, cyanobacteria, spirochaetes, green sulfur bacteria, green non-sulfur bacteria, and respiratory symptoms *Moraxella*. In some embodiments, said bacteria is selected from the group consisting of *Escherichia coli, Staphylococcus aureus, Pseudomonas aeruginosa* and *Enterococcus hirae*. In some embodiments, said fungus is selected from the group consisting of *Magnaporthe, Ophiostoma, Cryphonectria, Fusarium, Ustilago, Alternaria, Cochliobolus, Aspergillus, Candida, Cryptococcus, Histoplasma*, and *Pneumocytis*. In some embodiments, said yeast is selected from the group consisting of *Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae* and *Rhodotorula mucilaginosa*. In some embodiments, said virus is selected from the group consisting of Adenoviruses, Herpesviruses, Poxviruses, Parvoviruses, Reoviruses, Picornaviruses, Togaviruses, Orthomyxoviruses, Rhabdoviruses, Retroviruses and Hepadnaviruses.

In some embodiments, by said contacting said composition kills at least one of an insect, an arachnid and a nematode. In some embodiments, said insect is selected from the group consisting of Blattodea, Coleoptera, Dermaptera, Diptera, Embioptera, Grylloblattaria, Hymenoptera, Lepidoptera, Mantodea, Mecoptera, Megaloptera, Neuroptera, Orthoptera, Phasmatodea, Phthiraptera, Plecoptera, Siphonaptera, Strepsiptera, Trichoptera, Zoraptera, Zygentoma, Ephemeroptera, Odonata, Thysanura, Monura, and Archaeognatha. In some embodiments, said insect is an immature insect. In some embodiments, said insect is in the egg stage, the larval stage or the pupal stage. In some embodiments, said insect is a mature insect. In some embodiments, said arachnid is a member of the group Acarina. In some embodiments, said nematode is selected from the group consisting of *Ascaris, Filaria, Ancylostoma*, and *Necator, Enterobius Trichuris, Trichinella, Baylisascaris, Dirofilaria, Haemonchus, Aphelenchoides, Ditylenchus, Globodera, Heterodera, Longidorus, Meloidogyne, Nacobbus, Pratylenchus, Trichodorus, Xiphinema* and *Bursaphelenchus*.

In some embodiments, by said contacting said composition kills a rodent. In some embodiments, by said contacting said composition kills a weed or foliage or prevents its growth.

In some embodiments, the mass of performic acid (PFA) which is contacted with said edible matter or substrate therefor is not more than 0.001 times the mass of the edible matter or substrate therefor. In some embodiments, the mass of PFA which is contacted with said edible matter or substrate therefor is not more than 0.0001 times the mass of the edible matter or substrate therefor. In some embodiments, the mass of PFA which is contacted with said edible matter or substrate therefor is not more than 0.00001 times the mass of the edible matter or substrate therefor.

In some embodiments, the ratio of the mass of PFA which is contacted with said edible matter or substrate therefor to the surface area of said edible matter or substrate therefor is not more than 1 mg per 100 $cm^2$. In some embodiments, the ratio of the mass of PFA which is contacted with said edible matter or substrate therefor to the surface area of said edible matter or substrate therefor is not more than 1 mg per 500 $cm^2$. In some embodiments, the ratio of the mass of PFA which is contacted with said edible matter or substrate therefor to the surface area of said edible matter or substrate therefor is not more than 1 mg per 1000 $cm^2$. In some embodiments, the ratio of the mass of PFA which is contacted with said edible matter or substrate therefor to the surface area of said edible matter or substrate therefor is not more than 1 mg per 5000 $cm^2$. In some embodiments, the ratio of the mass of PFA which is contacted with said edible matter or substrate therefor to the surface area of said edible matter or substrate therefor is not more than 1 mg per 10000 $cm^2$. In some embodiments, the ratio of the mass of the PFA which is contacted with said edible matter or substrate therefor to the volume of said edible matter or substrate therefor is not more than 1 g per 0.1 $m^3$. In some embodiments, the ratio of the mass of the PFA which is contacted with said edible matter or substrate therefor to the mass of said edible matter or substrate therefor is not more than 1 g per 0.3 $m^3$. In some embodiments, the ratio of the mass of the PFA which is contacted with said edible matter or substrate therefor to the mass of said edible matter or substrate therefor is not more than 1 g per 0.5 $m^3$. In some embodiments, the ratio of the mass of the PFA which is contacted with said edible matter or substrate therefor to the mass of said edible matter or substrate therefor is not more than 1 g per 1 $m^3$.

In some embodiments, the PFA is brought into contact with said edible matter by immersing the edible matter in the composition. In some embodiments, the PFA is brought into contact with said edible matter by spraying the composition on said edible matter. In some embodiments, the PFA is brought into contact with said edible matter by fogging the edible matter with the composition. In some embodiments, the PFA is in the gas phase when it is brought into contact with said edible matter. In some embodiments, the PFA is generated in the fog or the gas phase by creating a PFA source-containing fog or gas, and bringing said PFA source-containing fog or gas into contact with ozone in the presence of said edible matter. In some embodiments, said ozone in gaseous. In some embodiments, said ozone is dissolved in water. In some embodiments, the performic acid is brought into contact with a substrate for the edible matter, which is subsequently brought into contact with said edible matter. In some embodiments, the composition is prepared in accordance with any of original claims 107 to 111. In some embodiments, the edible matter is not a plant oil that is still in edible form. In some embodiments, the edible matter is not fully cooked, e.g. the edible matter is uncooked or only partially cooked.

There is also provided, in accordance with an embodiment of the invention, an aqueous composition containing (1) water, (2) at least one of (a) phosphonic acid (HP(O)(OH)$_2$) or a salt thereof and (b) phosphoric acid, (3) a carboxylic acid, (4) a surfactant, and (5) at least one of a performic acid source and an oxidizer which can oxidize said performic acid source to performic acid.

In some embodiments, the carboxylic acid is present in a concentration of 0.5 to 42 wt. %. In some embodiments, the carboxylic acid is present in a concentration of 0.5 to 1 wt. %. In some embodiments, the carboxylic acid is present in a concentration of 10 to 42 wt. %. In some embodiments the carboxylic acid contains from 2 to 7 carbon atoms. In some embodiments the carboxylic acid is selected from the group consisting of citric acid, propionic acid, lactic acid, salicylic acid, benzoic acid, glyceric acid, oxalic acid, tartaric acid, acetic acid, chloroacetic acid, dichloroacetic acid, trichloroacetic acid, and trifluoroacetic acid. In some embodiments the carboxylic acid is provided as a mixture of carboxylic acids. In some embodiments, the composition contains phosphonic acid, a salt thereof, or a mixture of phosphonic acid and a salt thereof in a concentration of 0.5 to 98 wt. %. In some embodiments, said phosphonic acid, salt thereof or mixture of phosphonic acid and a salt thereof is present in a concentration of 0.5 to 1 wt. %. In some embodiments, said phosphonic acid, salt thereof or mixture of phosphonic acid and a salt thereof is present in a concentration of 10 to 98 wt. %. In some embodiments, said salt is a salt selected from the group consisting of potassium, sodium or ammonium salt. In some embodiments, prior to addition to the aqueous composition, the phosphonic acid has been at least partly neutralized. In some embodiments, said phosphonic acid has been at least partly neutralized by addition of KOH. In some embodiments, said surfactant is present in a concentration of 0.001 to 10 wt. %. In some embodiments, said surfactant is present in a concentration of 1 to 10 wt. %. In some embodiments, said surfactant is present in a concentration of 0.001 to 0.1 wt. %. In some embodiments, said surfactant is an alkyl polyglycoside. In some embodiments, said performic acid source is present in a concentration of 0.25 to 98 wt. %. In some embodiments, said performic acid precursor is present in a concentration of 10 to 98 wt. %. In some embodiments, said performic acid precursor is present in a concentration of 0.25 to 1 wt. %. In some embodiments, said performic acid source is selected from the group consisting of formic acid, formic acid esters, and formic acid salts. In some embodiments, said phosphoric acid is present in a concentration of 0.00001 to 98 wt. %. In some embodiments, said phosphoric acid is present in a concentration of 0.00001 to 1 wt. %. In some embodiments, said phosphoric acid is present in a concentration of 10 to 98 wt. %. In some embodiments, said oxidizer is present in a concentration of 0.5 to 70 wt. %. In some embodiments, said oxidizer is present in a concentration of 10 to 70 wt. %. In some embodiments, said oxidizer is present in a concentration of 0.5 to 1 wt. %. In some embodiments, said oxidizer is selected from the group consisting of inorganic peroxides, nitrates, halogens and halogen compounds, hypohalite compounds, ozone, oxides, permanganate salts, multi-valent chromium compounds, acids, sulfides and Tollens' reagent. In some embodiments, the oxidizing agent is selected from the group consisting of hydrogen peroxide, sodium percarbonate, sodium periodate, sodium persulfate, ammonium persulfate, sodium perborate, sodium peroxide, calcium peroxide, silver (II) oxide, chlorine dioxide, diacyl peroxides, ketone peroxides, peroxydicarbonates, peroxyesters, dialkyl peroxides, hydroperoxides, peroxyketals, urea hydrogen peroxide, ammonium hydrogen peroxide, ozone, sodium peroxydisulfate, potassium peroxydisulfate and ammonium peroxydisulfate. In some embodiments, the composition further comprises performic acid. In some embodiments, the concentration of said performic acid is from 1 ppb to 50 wt. %. In some embodiments, the concentration of said performic acid is from 5 to 50 wt. %. In some embodiments, the concentration of said performic acid is from 1 ppb to 1000 ppm. In some embodiments, the composition does not contain said oxidizer. In some embodiments, the composition does not contain a performic acid source or performic acid. In some embodiments, the composition contains performic acid and in which the concentration of performic acid therein decreases by not more than 1% over 6 months at a temperature below 20° C. In some embodiments, the concentration of performic acid therein decreases by not more than 1% over 6 months at a temperature of 20° C.

In some embodiments, the composition is such that at a concentration of 20 ppm performic acid and a contact time of one minute at room temperature, the composition achieves a 10000-fold (4 log) reduction in the cfu of a pathogen grown on a designed growth medium, wherein the pathogen is at least one of the pathogens selected from the group consisting of *Escherichia coli* (ATCC 8739), *Staphylococcus aureus* (ATCC 6538), *Pseudomonas aeruginosa* (ATCC 9027), *Enterococcus hirae* (ATCC 10541), *Candida albicans* (ATCC 10231), *Aspergillus niger* (ATCC 16404), *Listeria monocytogenes* (ATCC 19115) and *Penecillium* w.t. (wild type). In some embodiments, the composition is such that at a concentration of 20 ppm performic acid and a contact time of one minute at room temperature, the composition achieves a 100000-fold (5 log) reduction in the cfu of a pathogen grown on a designed growth medium, wherein the pathogen is at least one of the pathogens selected from the group consisting of *Escherichia coli* (ATCC 8739), *Staphylococcus aureus* (ATCC 6538), *Pseudomonas aeruginosa* (ATCC 9027), *Enterococcus hirae* (ATCC 10541) and *Listeria monocytogenes* (ATCC 19115). In some embodiments, with a one-minute contact time the composition meets or exceeds at least one of the British Standards BS EN 1276:1997 and BS EN 1276:2009. In some embodiments, the composition exceeds British Standard BS EN 1276:1997. In some embodiments, the composition possesses bactericidal activity within one minute at 20° C. under dirty conditions of 3.0 g/l bovine albumin for at least one of the reference strains *E. coli* (ATCC 8739), *Staphylococcus aureus* (ATCC 6538), *Pseudomonas aeruginosa* (ATCC 9027), *Listeria monocytogenes* (ATCC 19115) and *Enterococcus hirae* (ATCC 10541). In some embodiments, the composition possesses bactericidal activity within one minute at 20° C. under dirty conditions of 3.0 g/l bovine albumin for the reference strains *E. coli* (ATCC 8739), *Staphylococcus aureus* (ATCC 6538), *Pseudomonas aeruginosa* (ATCC 9027), and *Enterococcus hirae* (ATCC 10541). In some embodiments, the composition exceeds at least one of British Standards BS EN 1650:1998 and BS EN 13697:2001. In some embodiments, the composition possesses fungicidal activity within one minute at 20° C. under dirty conditions of 3.0 g/l bovine albumin for at least one of the reference strains *Candida albicans, Aspergillus brasiliensis (Aspergillus niger)*, and *Penecilium* w.t. In some embodiments, the composition possesses fungicidal activity within one minute at 20° C. under dirty conditions of 3.0 g/l bovine albumin for the reference strains *Candida albicans, Aspergillus brasiliensis (Aspergillus niger)*, and *Penecilium* w.t. In some embodiments, except for performic acid and the ingredients listed in original claim 61, the composition is substantially free of other microbicides and fungicides.

There is also provided, in accordance with an embodiment of the invention, a method for making a composition in accordance with embodiments of the invention, including a composition according to any one of original claims 61 to 106, which comprises (a) mixing, not necessarily in the following order, (1) water, (2) at least one of (i) phosphonic acid $(HP(O)(OH)_2)$ or a salt thereof and (ii) phosphoric acid, (3) a carboxylic acid, (4) a surfactant, and (b) one of a performic acid source and an oxidizer which can oxidize the performic acid source to performic acid; and (b) thereafter mixing into the mixture the other of the performic acid source and the oxidizer, whereby to generate a composition containing performic acid. In some embodiments, all of said mixing steps in (a) take place in the liquid phase. In some embodiments, the mixing in (b) takes place in the liquid phase. In some embodiments, the oxidizer is ozone and the mixing in (b) takes place in the gas phase. In some embodiments, the oxidizer is ozone and the mixing in (b) takes place when said ozone is dissolved in water.

There is also provided, in accordance with an embodiment of the invention, edible matter having performic acid therein or thereon in an amount of not more than 1 ppm relative to the total amount of edible matter; such concentrations may be determined by standard methods used in the art. In some embodiments, the edible matter which has been treated in accordance with a method according to any one of original claims 1 to 60. In some embodiments, the edible matter has performic acid therein or thereon in an amount of not more than 1 ppm relative to the total amount of edible matter. There is also provided, in accordance with an embodiment of the invention, edible matter having silver therein or thereon in a detectable amount but not exceeding than 1 ppb relative to the total amount of edible matter. In some embodiments, the edible matter on or in which the performic acid and/or silver is present is selected from the group consisting of fruits, vegetables, grains, sprouts, nuts, seeds, meats, meat products, milk, milk products, fish, poultry, eggs, and mixtures thereof. In some embodiments, the edible matter is selected from the group consisting of apple, avocado, citrus—mandarin, citrus—orange, citrus—mineola, citrus—grapefruit, citrus—lemon, date, kiwi, lychee, mango, peach, pear, persimmon, pomegranate, pepper, asparagus, banana, broccoli, cabbage, carrot, cauliflower, celery, corn, kohlrabi, cucumber, eggplant, garlic, lettuce, onion, peanut, potato, strawberry, sweet pepper, sweet potato, tomato, watermelon, and grape. In some embodiments, the edible matter is a plant oil that is still in edible form. In some embodiments, the edible matter is not fully cooked, e.g. the edible matter is uncooked or only partially cooked.

According to certain embodiments of the invention, there are provided methods for treating edible matter or a substrate therefor. For example, according to certain embodiments, a method for treating edible matter comprises applying a composition comprising performic acid to the edible matter or a substrate therefor.

Methods according to various embodiments of the invention may entail treating edible matter at one or more stage(s) in the life-cycle of the edible matter, including, for example, pre-seeding stages, growth, harvest, and post-harvest processing, storage and transport, up through consumption and/or destruction of the edible matter.

As discussed elsewhere herein, according to certain embodiments the treating of edible matter may comprise applying the treating composition directly to the edible matter and/or applying the treating composition to substrates for the edible matter, including vessels, such as storage containers (e.g. warehouses, silos, boxcars, sheds, crates). Such substrates further include, for example, earth, other growth media, and other surfaces or areas, including equipment (e.g., for harvesting, packaging, processing), spaces (e.g., within processing equipment or storage containers), and other surfaces that may come in contact with or in proximity to edible matter.

The present inventor has found that treatment of edible matter with performic acid has utility in one or more respects, depending on the edible matter being treated. Thus, in accordance to with some embodiments, performic acid-containing compositions may be used to prevent or inhibit qualitative and/or quantitative losses of edible matter, for example, by applying an effective amount of such a composition to impart increased storage stability or extend shelf life to the edible matter.

Further, performic acid can decompose to $CO_2$ after application, and thus, in comparison to fungicides, microbicides and the like that leave residues on crops, soil and in groundwater, is environmentally friendly; consequently, in some embodiments, the performic acid or the performic acid-containing composition is not washed off the thing to which it is applied, e.g. edible matter or a substrate therefor, after its application thereto. Moreover, this decomposition product, $CO_2$, may function as a nutrient for plants. Thus, in some embodiments, the method may simultaneously treat plants (e.g. to prevent decay or losses by, for instance, disinfecting or killing insects) and provide nutrients thereto, in a single application. Accordingly, in some embodiments, the method comprises providing $CO_2$ and/or other nutrients to the edible matter, e.g., growing vegetative matter, for example via decomposition of at least some of the performic acid, or other component, in an amount useful for providing nutrients to the edible matter. In some cases, $CO_2$ generated by performic acid decomposition may function as an insecticide, acaricide or nematocide or otherwise act to reduce insect, acarid or nematode infestation. For example, in stored grains or legumes, an increase in the $CO_2$ concentration in the atmosphere of the storage container (such as a silo) to several percent, which is several times the natural occurrence of $CO_2$, may inhibit the functioning of such organisms. In some embodiments, the performic acid may be generated in part using materials, such as potassium bicarbonate, that themselves degrade to release $CO_2$.

Performic acid is often unstable and sometimes even explosive. Accordingly, in accordance with some embodiments, rather than preparing the performic acid composition in advance or transporting it from a manufacturer to the site of use, it can be prepared at or near the site of use, and/or at or near the time of use. For example, according to some embodiments, the performic acid composition can be prepared by, for instance, combining a performic acid source with an oxidizing agent, and this can be done, according to certain embodiments, at or near the site of use, and/or at or near the time of use. Conversely, as will be explained in greater detail below, there are provided in accordance with some embodiments of the invention stable performic acid-containing compositions that exhibit stability for days, weeks or even months, and there are also provided in accordance with some embodiments of the invention pre-mixes for forming performic acid that can be transported and mixed on-site with other ingredients to generate performic acid-containing compositions.

According to some embodiments, there are provided methods of preventing decay of edible matter. For example, a composition comprising performic acid may be applied in an amount and for a time sufficient to prevent decay of the edible matter. As used herein, "decay" is understood to mean, inclusively, qualitative or quantitative loss. Naturally, the type of loss can depend not only on the type of edible matter, such as plant or meat, but also the life-cycle stage of the edible matter, such as pre-seed, growth, post-harvest or post-slaughter, etc. Some types of decay are not dependent on the stage of life-cycle of the edible matter. The decay of certain types of edible matter includes, for example, rotting, blackheart formation, losses from infection with microorganisms or losses from higher organisms, such as insects and rodents. Some types of decay are more prevalent during storage of the edible matter. As used herein, storage includes any stage before or after the edible matter is naturally propagated, such as pre-planting or post-harvest or post-slaughter; as used herein, it also includes periods of storing, for instance in boxes, silos, vessels, etc., transporting, packaging, processing, and distribution. During storage and depending on the type of edible matter, decay may be manifested, for example, as decomposing, rotting, sprouting (e.g. of potatoes), blossoming, germinating, and rooting, dehydrating, in addition to the aforementioned types of decay. It will be appreciated the that the term "prevent" and similar terms such as "protect" are not meant in an absolute sense, but rather that treatment of edible matter with performic acid or a composition as described herein may be used to delay, retard, slow or reduce the speed and/or degree of decay that otherwise would occur in the edible matter without such treatment. It will also be understood that the expression "edible matter which is not fully cooked" includes edible matter that has been flash-pasteurized.

In some embodiments, compositions containing performic acid may be useful as sanitizers, disinfectants and/or sterilizers, and accordingly there are provided methods of sanitizing, disinfecting, and/or sterilizing edible matter or a substrate therefor using a performic acid containing composition. For example, the methods may comprise applying one or more performic acid-containing composition(s) that are effective cleaners, antiseptics, sanitizers, disinfectants, and/or sterilizers. Thus, according to some embodiments, each of the one or more compositions, such as a composition comprising an effective concentration of performic acid, or a performic acid source and an oxidizing agent, can be applied to the edible matter or its substrate in an amount effective to sanitize, disinfect, and/or sterilize the edible matter or substrate(s) therefor.

In some embodiments, there are provided methods of destroying or controlling microorganisms in, on or near edible matter a substrate therefor. For example, such a method may comprise applying one or more compositions, such as a composition comprising an effective concentration of performic acid or a performic acid source and an oxidizing agent, that are effective as nematodecides, miticides, acaricides, fungicides, algaecides, bactericides, virucides, sporicides, anti-yeast agents, and/or an anti-bacteriophages. Thus, according to certain embodiments, each of the one or more compositions can be applied in an amount effective to destroy, reduce, or control nematodes, mites, ticks, fungi, algae, bacteria, viruses, spores, yeast, and/or bacteriophages when applied to the edible matter or substrate(s) therefor.

In some embodiments, there are provided methods of controlling or destroying harmful higher organisms, such as insects, rodents and weeds, in or near edible matter or a substrate therefor. This may comprise applying one or more formic acid-containing compositions that are effective insecticides, rodenticides, and/or herbicides. Thus, in accordance with some embodiments, each of the one or more compositions may be applied in an amount and for a time effective to destroy, reduce, or control insects, rodents, and/or plants, such as weeds, when applied to edible matter or substrates therefor. In at least one embodiment, the method comprises applying an amount of one or more compositions, such as a composition comprising an effective concentration of performic acid or a performic acid source and an oxidizing agent, effective as a herbicide. For example, herbicide activity can be useful to prevent or destroy weeds. In general, herbicidal activity is achieved at higher concentrations and application volumes than are necessary or used in treatments of edible matter to kill pathogens and the like.

In some embodiments, the applying comprises applying an amount of one or more of the compositions, such as a composition comprising an effective concentration of performic acid or a performic acid source and an oxidizing agent, effective to control, prevent, inhibit, eliminate or reduce at least one of decomposing, rotting, and black heart formation. In some embodiments, when the edible matter is in storage, the applying comprises applying an amount of one or more of the compositions effective to control, prevent, inhibit, eliminate, or reduce sprouting, blossoming, germinating, rooting, or dehydrating of the edible matter. In some embodiments, the applying comprises applying an amount of one or more of the compositions effective to control, prevent, inhibit, eliminate or reduce infection or disease in the edible matter, for instance at any stage of the life cycle of the edible matter. For example, in some embodiments, the applying comprises applying an amount of one or more of the compositions effective to control, prevent, inhibit, eliminate or reduce contamination by various pathogens.

In some embodiments, for instance in fruit and vegetable applications, the applying comprises adding an amount of one or more of the compositions, such as a composition comprising an effective concentration of performic acid or a performic acid source and an oxidizing agent, effective to control, prevent, inhibit, eliminate or reduce pathogens, such as seed-borne diseases, soil-borne diseases, water-borne diseases and/or air-borne diseases, and/or insects that act as vectors for and therefor spread such diseases.

In some embodiments, the performic acid or the composition is applied to edible matter contained in a storage vessel, or to the storage vessel itself, and the edible matter is retained in the storage vessel for a period of at least 1 day, at least 2 days, at least 3 days, at least 4 days, at least 5 days, at least 6 days, at least 7 days, at least one week, at least two weeks, at least three weeks, at least four weeks, at least five weeks, at least six weeks, at least seven weeks, or at least eight weeks after such application. In some embodiments the storage vessel is not moved after the performic acid is applied to the edible matter therein and/or to the storage vessel itself. In some embodiments, the storage vessel is an immobile storage vessel.

In accordance with some embodiments, the method comprises arresting, reducing or reversing sprouting of edible matter, for instance, sprouting of tubers, such as potatoes or sweet potatoes, for example while in storage, by applying, for example, a composition comprising an effective concentration of performic acid or a performic acid source and an oxidizing agent. Arresting sprouting includes stopping or slowing the elongation of sprouts as well as the shortening of the length of sprouts relative to the length of sprouts of untreated tubers. In some embodiments, the sprouting of tubers may be reversed, such that the total amount or degree of sprouting, such as due to sprouting during storage, is reduced.

In some cases, it may also be desirable to store edible matter under modified atmosphere conditions, e.g., at high relative humidity (RH) or in wherein the concentration of $CO_2$ is modified or controlled relative to the natural concentration of $CO_2$ in the air. Thus, in embodiments, it may be desirable to store edible matter in conditions of high RH and/or under a controlled atmosphere without incurring at least one of sprouting, rooting and/or black-heart formation of potatoes.

In some cases, for instance in applications involving tubers, such as potatoes, and roots, such as carrots or sweet potatoes, it may be desirable to enable edible matter to be stored in conditions of high relative humidity (RH), e.g., RH from 50% to 99+% while preventing decay that otherwise tends to occur due to or be accelerated by the storage conditions. Storage at high RH can provide the benefit of, for example, preventing weight loss by dehydration during storage, in some instances even for extended periods of time. For example, dehydration during storage is one of the major sources of weight loss in potatoes; such weight loss of the stored product translates directly to an economic loss. Moreover, water losses, for example from stored potatoes, can make edible matter undesirably soft, or more vulnerable to bruising, pathogenic attack and decay. However, known methods for storing potatoes at high RH generally promote sprouting and rooting, and often favor the growth of undesirable pathogens leading to qualitative and quantitative losses.

In some embodiments, the method comprises storing or maintaining the edible matter at high RH without incurring significant quantitative or qualitative losses. For instance, by treating the edible matter before and/or during storage with a performic acid containing composition, it is possible in accordance with some embodiments to store or maintain the edible matter at high RH and, simultaneously, at relatively high temperature, e.g., with a relatively little refrigeration (as opposed to a high degree of refrigeration), without incurring significant quantitative or qualitative losses. This could, for instance, provide significant energy savings over the lower temperature refrigeration that is usually required for storage of edible matter, particularly under conditions of high RH.

Thus, in some embodiments, the method comprises applying to the edible matter or its substrate a composition, such as a composition comprising an effective concentration of performic acid or a performic acid source and an oxidizing agent, under conditions of high RH and/or otherwise controlled atmosphere. The RH may be, for example, at least 50%, at least 55%, at least 60%, at least 65%, at least 70%, at least 75%, at least 80%, at least 85%, at least 90% or at least 95%. The RH can be, for example, from 50% to 100%. For instance, in some embodiments, the RH ranges from 60% to 98%, such as from 70% to 95%.

Depending on the type of edible matter, it can be stored at cold temperatures in order to reduce or control decay. However, such cold storage incurs costs, and cold storage is not available in all locations. According, in some embodiments, the method comprises applying a performic acid containing composition to reduce or control decay at elevated temperatures, e.g., above their typical cold storage conditions. For example, onions can be stored at around 0.5° C. to 1° C. to reduce or control decay, but at higher temperatures, such as ambient temperatures, can be treated as described herein to also reduce or control decay without cold storage, or with storage at a higher temperature. Similarly, certain types of table potatoes, which otherwise would be stored at 3° C., may be treated as described herein to additionally reduce or control decay at a storage temperature which is not as cold, such as at 7 or 8° C., which is more cost effective and environmentally friendly. Thus there is also provided in accordance with embodiments of the invention a method for improving the storage of edible matter, comprising contacting the edible matter or a substrate therefor with performic acid, and then storing the edible matter either (a) at low-temperature conditions typically used for the storage of such edible matter, but for a period of time longer than such low-temperature conditions generally facilitate, or (b) for a period of time that is usually facilitated by low-temperature conditions, but at a temperature higher than is typically required for storage of the edible matter for such a period of time.

In some embodiments, application of performic acid containing compositions can be used to enhance or strengthen the resistance of a living plant to external forces. For example, the method may enhance or strengthen the resistance of a plant to insects, or disease. By "enhance or strengthen the resistance of a plant", is meant the enhancement or strengthening of resistance of a plant's native or natural ability to maintain its health. For example, agents that strengthen a plant's resistance, such as salicylic acid or certain essential oils, which can stimulate a plant's immune system, can be used. Thus, in some embodiments, the composition comprises an effective concentration of performic acid or a performic acid source and an oxidizing agent and an agent for increasing such resistance, such as salicylic acid or certain essential oils, such as caraway oil, *capsicum* oil, citronella oil, clove oil, dill oil, *eucalyptus* oil, limonene or D-limonene, grapefruit oil, lemon oil, lemongrass oil, lime oil, mint oil, oregano oil, peppermint oil, pine oil, rosemary oil, spearmint oil, and tea tree oil. The agent to enhance resistance can, according to certain embodiments, provide additional functions as well. For example, salicylic acid can also provide pH regulation to the composition(s). In some embodiments, the salicylic acid may be combined with an alcohol, which may provide further benefits, e.g. regeneration of performic acid and/or formic acid by reaction with carbon monoxide released when performic acid and/or formic acid decompose. Thus, in some embodiments, the method may enhance or strengthen resistance of a plant to external forces when the plant lacks genetic modification used to enhance or strengthen or strengthen such resistance, i.e., a natural plant. For instance, the agent to enhance resistance can be applied at any stage during the life cycle of the plant, including to seeds, during growth of the plant, or post-harvest. According to still further embodiments, the method also may enhance or strengthen resistance of a genetically-modified plant to external forces, wherein the genetic modification is used to enhance or strengthen such resistance.

As used herein, "performic acid source" is understood to mean any material that can be oxidized to produce performic acid. Furthermore, the term "performic acid containing composition" will be understood as including both a composition that comprises performic acid, as well as a combination that includes a performic acid source and an oxidizing agent; the latter may be, for example, an aqueous solution containing e.g. (1) formic acid and (2) $H_2O_2$ and/or $O_3$ (which will result in formation of performic acid in the solution), or it may be an aqueous composition containing formic acid which when fogged or gassed onto fruits, grains and the like or into enclosed spaces in an ozone-rich atmosphere results in formation of performic acid in such spaces and on surfaces exposed to the fog or gas, including surfaces of fruits, grains and the like as well as the walls of such enclosed spaces, such as storage rooms, silos, hospital rooms, train cabins, airplane cabins, bus interiors or equipment therein, such as hospital equipment.

Exemplary performic acid sources include formic acid, formic acid esters, and formic acid salts, such as water soluble salts of formic acid, for instance, alkali metal formates, such as sodium formate and calcium formate, formaldehyde, formamide. For example, the performic acid source may comprise more than one substance, such as substances that combine to produce formic acid, formic acid esters, formamide, and the like. In some embodiments, the performic acid source comprises sulfuric acid and sodium formate; carbon monoxide and alcohol; methyl formate and ammonia; and/or formaldehyde and atmospheric oxygen. In one embodiment, the performic acid source comprises at least one of formic acid, salts of formic acid, and esters of formic acid.

In some embodiments, the performic acid source comprises formic acid as the sole performic acid source or, in other embodiments, as one of multiple performic acid sources. For example, the performic acid source may comprise formic acid in an amount ranging from 85% to 100%, by weight, relative to the total weight of the performic acid source, with the remainder being a performic acid source other than formic acid. In some embodiments, the performic acid source comprises formic acid in an amount ranging from 90% to 100%, by weight, such as from 95% to 100%, or from 99% to 100%, relative to the total weight of the performic acid source. In at least one embodiment, the performic acid source consists essentially of formic acid.

In some embodiments, the performic acid source comprises an ester of formic acid. Esters of formic acid include, for example, ethyl formate, methyl formate, propyl formate, and mixtures thereof. While useful according to certain embodiments, esters of formic acid have relative disadvantages with respect to, for example, the types of catalysts that can be used, which could affect reaction time and/or yield. Thus, selection of the performic acid source may be based, for example, on considerations of the desired catalyst and, for example, considerations relating to yield, reaction time, reaction robustness or explosivity concerns, the edible matter to be treated, and/or the manner of applying. Thus, in some embodiments, esters of formic acid are not used as the performic acid source, or are used in amounts less than 3%, by weight, such less than 2%, or less than 1%, relative to the total weight of the performic acid source.

In some embodiments, preparing a composition comprising performic acid comprises combining a performic acid source with an oxidizing agent. In at least one embodiment, the amount of performic acid source ranges from 1% to 20%, or from 1% to 15%, or 1% to 10%, 1% to 9%, 1% to 8%, 1% to 7%, 1% to 6%, 1% to 5%, 1% to 3%, or 1% to 2% by weight relative to the total weight of the composition in intermediate compositions, such as described in the examples below. The performic acid source can be used in much higher concentrations, for instance up to 99% by weight relative to the total weight, in intermediate compositions, such as those discussed herein.

According to certain embodiments, the amount and type of the performic acid source and the amount and type of the oxidizing agent may be sufficient to produce performic acid. For example, according to certain embodiments, amounts and types of the performic acid source and oxidizing agent may be sufficient to produce performic acid in an amount and/or a concentration (e.g. 1 ppb to 40 wt. %) to provide the desired function, e.g., disinfecting, or prevent the decay of the edible matter. For example, according to certain embodiments, amounts and types of the performic acid source and oxidizing agent may be sufficient to produce performic acid in an amount of greater than 10 ppm. The concentration of performic acid can be measured, for example, by the method disclosed in Gehr et al., Performic Acid (PFA): Tests on advanced primary effluent shows promising disinfection performance, WST 59.1, p. 89-96 (2009).

For instance, the type of performic acid source may be chosen based on compatibility with other components of the composition, such as catalysts. Additionally, the performic acid source, in some embodiments, may provide additional functions or characteristics to the composition, such as herbicidal properties, or corrosive properties that may be advantageous, for instance, in treating substrates, foliage or sprouts. For example, at the end of potato growth period, such as after 100 days, potato foliage should be destroyed to prevent further excessive growth, and this result can be achieved, according to certain embodiments, at least where the performic acid source comprises formic acid. Or, for example, the performic acid source may, in addition to being a source for performic acid, function to reduce or control weed growth.

In some embodiments, the composition may comprise at least one additive. For example, according to certain embodiments, the method comprises combining or using together the least one additive and the performic acid source and the oxidizing agent.

Combining, as used herein, can be simultaneous or sequential, including adding different components at different times and/or in the same composition or in multiple compositions, which multiple compositions can be combined. In this regard, a composition may be prepared by preparing one or more intermediate compositions.

According to various embodiments, any additive useful in compositions relating to treating edible matter or its substrates may be used. For example, the additive may be at least one of a disinfectant, surfactant, antifoaming agent, anti corrosion agent, coloring agent, odorant, lubricant, essential oil, emulsifier, homogenizer, chelating agent, stabilizer, synergist, viscosity regulator, pH regulator, solvent, promoter, modifier, trace element activator, inorganic or organic additive, corrosion inhibitor, or flavoring agent. Of course, one additive may have more than one function or provide more than one property.

According to certain embodiments, a composition can comprise a pH regulator. A pH regulator may be used, for example, to control or stabilize the oxidizing of the performic acid source by the oxidizing agent. A pH regulator may be used, as another example, to provide additional functions, such as disinfecting. A pH regulator may be used, as yet a further example, to effect the pH of the composition when applied to the edible matter or its substrate, for instance so as to avoid or diminish any unwanted damage to or reaction with the edible matter or its substrate. The pH regulator may comprise, for example, at least one second acid, at least one base, and/or at least one pH buffer. Suitable pH regulators may be selected based on, for example, compatibility with other ingredients in the composition, the material to which the composition is to be applied, and/or the method of application, e.g., the application equipment.

For example, the pH regulator may comprise at least one second acid. As used herein, "second acid" is understood to mean an acid that is not performic acid or the performic acid source, regardless of whether or not the performic acid source is or is not an acid and regardless of whether or not the performic acid or the performic acid source affects the pH of the composition. Thus, the term "second acid" is used for definitional purposes and is not intended to imply that the composition necessarily comprises a first acid. Further, as discussed herein, the second acid may or may not be used to provide pH regulation.

As discussed above, suitable second acids may be selected based on, for example, compatibility with other ingredients in the composition, the material to which the composition is to be applied, and/or the method of application. As another example, the type and concentration of the second acid may be chosen based on its function in providing pH control, such as pH control depending on the other components and/or in view of the length of time between composition preparation and application, the type of edible matter or substrate, toxicity, the life-cycle stage, intended storage time or conditions, other components in the composition, and/or the manner of application, such as fogging or dipping, the duration of application, ambient conditions during application, etc. As another example, the type and concentration of a second acid may be chosen to provide additional function for treating edible matter or its substrate, such as disinfecting.

For example, the at least one second acid may be selected from mineral acids, sulfonic acids, carboxylic acids, vinylogous carboxylic acids, and nucleic acids, organic acids and inorganic acids, and may be monoprotic or polyprotic, or strong or weak. Exemplary second acids that may be used include, but are not limited to, phosphonic, phosphoric, sulfuric, nitric, oxalic, citric, tartaric, boric, bromic, stannic, peracetic, hydrochloric, salicylic, and sulfuric acid, hydrofluoric, hydrobromic, acetic, chloroacetic, dichloroacetic, trichloroacetic, trifluoroacetic, benzoic, lactic, uric, fluorosulfuric, hypochloric, chloric, perchloric, periodic, fluorosulfuric, fluoroantimoic, fluoroboric, chromic, methanesulfonic, ethanesulfonic, benzenesulfonic, ascorbic, deoxyribonucleic, ribonucleic, hydroiodic, and p-Toulenesulfonic acid.

According to certain embodiments, the second acid is or comprises a carboxylic acid.

In some embodiments, the second acid is selected from hydrochloric, phosphonic, phosphoric, sulfuric, nitric, oxalic, citric, tartaric, boric, bromic, stannic, peracetic, hydrochloric, salicylic, and sulfuric acid. In a further embodiment, at least one second acid is phosphonic acid.

In at least one embodiment, the second acid is present in the final or an intermediate composition in a concentration ranging from 10 ppm to 90% by weight relative to the total weight of the composition. For example, the second acid may be present in an amount ranging from 10 ppm to 70%, or from 10 ppm to 50%, such as from 10 ppm to 20%, or from 10 ppm to 10%, or from 10 ppm to 5%, or from 10 ppm to 1%, by weight relative to the total weight of the final or intermediate composition.

According to certain embodiments, the pH regulator may comprise at least one base. The type and concentration of base may be selected to be, for example, compatible with other ingredients in the composition, based on the material to which the composition is to be applied, and/or the method of application, e.g., the application equipment. As another example, the base may be chosen to provide pH control, such as pH control depending on the other components and/or in view of the length of time between composition preparation and application, the type of edible matter or substrate, the life-cycle stage of the edible matter, intended storage time or conditions, and/or the manner of application, such as fogging or dipping, the duration of application, ambient conditions during application, etc. As another example, the base may be chosen to provide additional function for treating edible matter or its substrate, such as disinfecting.

For example, the at least one base may be selected from hydroxides, such as lithium hydroxide, sodium hydroxide (caustic soda or lye), potassium hydroxide, rubidium hydroxide, cesium hydroxide, calcium hydroxide, strontium hydroxide, barium hydroxide; caustic soda, ureas, carbonates, ammonia, alanine, amines, such as dimethylamine, ethylamine, glycine, hydrazine, methylamine, trimethylamine, pyridine, or ammonium hydroxide. In one embodiment, the at least one base is chosen from caustic soda, ammonia, and urea.

In some embodiments, the pH regulator comprises one or more buffers. The type and concentration of buffer and buffer components may be selected to be, for example, compatible with other ingredients in the composition, based on the material to which the composition is to be applied, and/or the method of application, e.g., the application equipment. For example, the buffer may comprise one or more of citric acid buffers, glycine buffers, acetic acid buffers, cacodylic acid buffers, bicarbonate buffers, pipes buffers, tris buffers, imidazole buffers, phosphate buffers, triethanolamine buffers, taps buffers, boric acid buffers, and piperidine buffers. For instance, the buffer may comprise hydrochloric acid and potassium chloride; glycine and hydrochloric acid; potassium hydrogen phthalate and hydrochloric acid; citric acid and sodium citrate; sodium acetate and acetic acid; potassium hydrogen phthalate and sodium hydroxide; disodium hydrogen phthalate and sodium dihydrogen orthophosphate; dipotassium hydrogen phthalate and potassium dihydrogen orthophosphate; barbitone sodium and hydrochloric acid; sodium tetraborate and hydrochloric acid; glycine and sodium hydroxide; sodium tetraborate and sodium hydroxide; sodium hydrogen orhotphosphate and sodium hydroxide; potassium chloride and sodium hydroxide; or mixtures thereof.

In some embodiments, the pH regulator adjusts the pH of the composition to a pH ranging from 0.1 to 8. For example, the second acid can adjust the pH of the composition to a pH ranging from 0.1 to 7, or in some embodiments, to a pH ranging from 0.1 to 6, or from 0.1 to 5, or from 0.1 to 3, or from 0.1 to 2, or from 0.1 to 1. For example, according to certain embodiments, a pH of from 0.1 to 3 has been found particularly useful to stabilize the composition without causing substantial losses of the edible matter treated.

In some embodiments, the at least one additive comprises at least one essential oil. The type and concentration of essential oil may be selected based on, for example, the desired properties of the essential oil, toxicity of the essential oil, compatibility with other ingredients in the composition, based on the material to which the composition is to be applied, and/or the method of application, e.g., the application equipment. Essential oils are generally volatile, liquid aroma compounds derived from natural sources, such as from plants, and are typically, but not always, poorly soluble in water. According to some embodiments, the type and concentration of essential oil may be used, for example, to provide enhanced or additional characteristics to the composition, such as anti-microbial, antiseptic, antiviral, herbicidal or insecticidal properties, fragrance, scent, medicinal characteristics, physical properties (e.g., viscosity) and/or flavor.

Exemplary essential oils include, but are not limited to, agar oil, allspice essential oil, ajwain oil, *angelica* root oil, anise oil, asafoetida, balsam oil, basil oil, bay, benzoin oil, bergamot oil, boldo oil, black pepper oil, buchu oil, birch oil, bitter almond oil, cajuput oil, calamus oil, camphor, *cannabis* flower oil, caraway oil, cardamom seed oil, carrot seed oil, *cassia* oil, catnip oil, cedarwood oil, chamomile oil, calamus root, cinnamon oil, cistus, citronella oil, clary sage oil, clove leaf oil, coffee, coriander, costmary oil, costus root, cranberry seed oil, cubeb, cumin oil, cypress oil, cypriol, curry leaf, davana oil, dill oil, eleni oil, elecampane, *eucalyptus* oil, fennel seed oil, fenugreek oil, fir, frankincense oil, galangal, *galbanum*, geranium oil, ginger oil, goldenrod, grapefruit oil, henna oil, helicrysum, horseradish oil, hyssop oil, Idaho tansy, jasmine oil, juniper berry oil, *laurus nobilis*, lavandin oil, lavender oil, limonene or D-limonene, ledum, lemon oil, lemongrass oil, lime oil, *litsea cubeba* oil, mandarin oil, manuka oil, marjoram, *melaleuca* (tea tree) oil), melissa oil (lemon balm), mint oil, mountain savory oil, mugwort oil, mullein oil, mustard oil, myrrh oil, myrtle oil, neem tree oil, neroli oil, niaouli oil, nutmeg oil, orange oil, oregano oil, orris oil, palo santo oil, palma rosa oil, parsley oil, patchouli oil, pennyroyal oil, *perilla* essential oil, peppermint oil, petitgrain oil, pimento oil, pine oil, ravensara oil, red cedar oil, roman chamomile, rose oil, rosehip oil, rosemary oil, rosewood oil, rue oil, sage oil, sandalwood oil, *sassafras* oil, saory oil, schisandra oil, spearmint oil, spikenard oil, spruce oil, star anise oil, *tagetes* oil, tansy oil, thuga oil, tuberose oil, tangerine oil, tarragon oil, thyme oil, *tsuga*, turmeric, vanilla oil, valerian oil, vetiver oil, western red cedar oil, wintergreen oil, wormwood oil, yarrow oil, ylang-ylang oil, and zedoary oil.

In at least one embodiment, the essential oil is chosen from at least one of caraway oil, citronella oil, clove oil, dill oil, *eucalyptus* oil, limonene or D-limonene, grapefruit oil, lemon oil, lemongrass oil, lime oil, mint oil, oregano oil, peppermint oil, pine oil, rosemary oil, spearmint oil, and tea tree oil.

The compositions can, in some embodiments, comprise stabilizers and/or viscosity modifiers. The type and concentration of stabilizers and/or viscosity modifiers may be selected based on, for example, compatibility with other ingredients in the composition, the material to which the composition is to be applied, and/or the method of application, e.g., the application equipment. Exemplary stabilizers and modifiers include, but are not limited to, citric acid, tartaric acid, boric acid, bromic acid, stannates, phosphoric acids, glycerin and silicone. A stabilizer and/or viscosity modifier can be used, for example, to slow down the decomposition of the formula. For instance, in some embodiments, a stabilizer may slow the reaction or decomposition of aperoxide and/or prolong the life of an oxidizing agent either before or after adding the composition to the edible matter. The amount and type of a stabilizer and/or modifier may be based on, for example the desired degree of stabilization or viscosity modification, the other components of the composition, the manner of applying, toxicity, and other desired characteristics.

In some embodiments, the stabilizer comprises phosphoric acid. In some embodiments, the stabilizer comprises phosphates, such as disodium phosphate (such as Dequest® 2010).

In some embodiments, the stabilizer and/or viscosity modifier may provide additional functions or benefits. For instance, phosphonic acid and/or phosphoric acid and/or some essential oils can stabilize an oxidant and can also be, in some embodiments, a disinfectant.

The compositions can optionally comprise one or more trace element activators to active the oxidizer; materials that act synergistically with the performic acid, performic acid source, oxidizer and/or other ingredients in the composition to provide improved efficacy; and/or promoters. Trace element activators, synergists and/or promoters can be used, for example, to increase or influence the initiation or rate or extent of a reaction, for instance, by influencing or initiating a reaction themselves or by activating a catalyst. Trace element activators, synergists and promoters include, but are not limited to, metals (e.g. elements listed in groups III through group XII of the periodic table), metal salts, metal oxides, metal dispersions, metal ions, metal ion dispersions, and dispersions comprising metal. For example, suitable trace element activators, synergists and promoters may include one or more of titanium, copper, zinc, nickel, iron, potassium, manganese, silver, chromium, molybdenum, and magnesium. Other activators may be boron, phosphorus, iodine, sulfur, citrate, or oxides thereof or salts thereof. The amount and type of the trace element activator(s), synergist(s) and/or promoter(s) may be based on, for example, the desired degree of activation, synergism and/or promotion, the other components of the composition, the type of edible matter, residues, toxicity, and manner of applying, and the like.

In some embodiments, the synergist and/or promoter comprise sulfuric acid.

In some embodiments, the synergist and/or promoter can provide additional functions or benefits. For instance, sulfuric acid can enhance performic acid production, and can also be, in some embodiments, a disinfectant and/or a pH regulator and/or a herbicide and/or a source of internal heat, for instance when heat is used to catalyze the oxidation.

The compositions can, in some embodiments, comprise at least one inorganic or organic additive. For example, but not by way of limitation, organic or inorganic additives may include, in addition to the aforementioned additives, peracetic acid, phenol, gelatin, glycerin, sodium azide, polymoxin B, sodium bicarbonate, pectin, salicylic acid, alcohols, ionic and nonionic adjuvants, surfactants, silicones, phosphates, phosphonates, etidronic acid (HEDP), and essential oils. Inorganic or organic additive can be used, for example, to enhance efficacy of the treatments. The types and amount of inorganic the desired degree of activation, synergism and/or promotion, the other components of the composition, the type of edible matter, residues, toxicity, and manner of applying.

In at least one embodiment, the composition comprises glycerin. Glycerin can be used, for example, to regulate viscosity, or may be used as a wetting agent, for instance to prolong the stability of the composition on the surface of the treated edible matter. For example, glycerin may slow or delay the evaporation of the composition from or near the surface or within the edible matter, increasing the contact time of the composition with the edible matter or the substrate, such as soil. For example, in some embodiments the composition may comprise glycerin in an amount ranging from 0% to 10%, by weight relative to the total weight of the composition, such as 0%, not more than 0.001%, not more than 0.01%, not more than 0.1%, not more than 1%, not more than 2%, not more than 3%, or from 0.1% to 9%, or from 0.1% to 8%, or from 0.1% to 7%, or from 0.1% to 6%, or from 0.1% to 5%, or from 0.1% to 4%, by weight relative to the total weight of the composition.

In some embodiments, the additive comprises one or more surfactants. Surfactants, for example, may lower the surface tension of the composition. Accordingly, the selection of surfactant may depend on the properties and components of the composition, the desired viscosity, the manner of application, toxicity, cost, and other properties of the surfactant. For example, the surfactant may provide other characteristics, functions, or properties to a composition, such as disinfectant properties. Suitable surfactants may be found among the cationic, anionic, non-ionic and amphoteric surfactants.

In some embodiments, the composition further comprises at least one solvent. The type and amount of solvent may be chosen, for example, based on the desired properties of the solvent, compatibility with other ingredients of the composition, the method of application, toxicity and environmental considerations, and the like. For example, in some embodiments, the solvent comprises at least one alcohol, such as acetic alcohol, methanol, and/or ethanol.

In addition to the aforementioned additives, other additives may be used in the compositions, depending on, for example, the desired properties of the composition. For instance, the additive may comprise one or more antifoaming agents, such as silicon or glycerin; corrosion inhibitor or anticorrosion agents, such as silicons or phosphates; coloring agents; odorants, such as essential oils; lubricants, such as gelatin or glycerin or silicone; emulsifiers, such as alcohols; homogenizers, such as alcohols, gelatin, glycerin, or sodium azide; chelating agents, such as phosphates, HEDP, or phosphonates; viscosity regulators, such as gelatin, glycerin, or pectin; flavoring agents, such as essential oils; and/or disinfectants, such as peracetic acid, sodium azide, salicylic acid, polymoxin B, or phenol; amphoteric agents, such as sodium bicarbonate. The amount and type of additive may be based on, for example, the other components of the composition, the type of edible matter, the residue of the additive, toxicity, manner of applying, environmental or regulatory considerations, etc. As discussed elsewhere in the application, some compounds may belong to one or more than one of these categories, and may have functions or properties other than the aforementioned.

In some embodiments, the pH of the composition comprising performic acid ranges from 0.1 to 8. For example, the pH of the composition may range from 0.1 to 7, or from 0.1 to 6, or from 0.1 to 5, or from 0.1 to 3, or from 0.1 to 2, or from 0.1 to 1. As discussed elsewhere herein, the pH of the composition may be controlled, according to certain embodiments, in order to, for example, do one or more of control or stabilize the oxidizing of the performic acid source by the oxidizing agent, provide additional functions, or avoid or diminish any unwanted damage to or reaction with the edible matter.

In some embodiments, the composition comprises or is formed using at least one oxidizing agent. The oxidizing agent can be any oxidizer compatible with the performic acid composition, for example capable of oxidizing the performic acid source to performic acid. Oxidizing agents are known in the art, and the type and concentration can be selected based on, for example, compatibility with various components, safety profile, and applicability under certain conditions (e.g., pH, temperature) and based on the present disclosure. The choice of oxidizing agent may depend on various factors, relating to the robustness of the oxidation required, the manner or mode of applying the edible matter, or the nature of the edible matter and intended applications. For instance, hydrogen peroxide and ozone are environmentally friendly, i.e., they inflict minimal or no harm on the environment, and are generally considered safe, as they decay and/or leave no toxic residue. Therefore, $H_2O_2$ and $O_3$ may be desirable as oxidizing agents in applications wherein the edible matter or its substrate is a food for human consumption, or soil for growing food sources for human consumption, etc. In some embodiments, the oxidizing agent is biodegradable, that is it will decompose by natural processes and chemical processes within the system into more basic components, for instance components containing carbon, hydrogen, and oxygen (water, carbon dioxide, and the like). For example hydrogen peroxide is generally biodegradable. In some embodiments, the oxidizing agent may provide one or more additional functions, such as disinfecting.

Oxidizing agents include, but are not limited to, inorganic peroxides, nitrates, halogens and halogen compounds, hypohalite compounds, ozone, oxides, permanganate salts, multivalent chromium compounds, acids, sulfides or Tollens' reagent. In at least one embodiment, the oxidizing agent is selected from hydrogen peroxide, sodium percarbonate, sodium periodate, sodium persulfate, ammonium persulfate, sodium perborate, sodium peroxide, calcium peroxide, silver (II) oxide, chlorine dioxide, diacyl peroxides, such as benzoyl peroxide, ketone peroxides, such as ((2,4-pentanedione peroxide), peroxydicarbonates, such as diisopropyl peroxydicarbonate, peroxyesters, dialkyl peroxides, hydroperoxides, such as t-butyl hydroperoxide, peroxyketals, such as 2,2-di(t-butyl peroxy) butane, urea hydrogen peroxide, ammonium hydrogen peroxide or ozone. In some embodiments, the oxidizing agent comprises one or more of sodium, potassium and ammonium peroxydisulfates. In at least one embodiment, the oxidizing agent comprises at least one of hydrogen peroxide, urea hydrogen peroxide, ammonium hydrogen peroxide, or ozone. According to certain embodiments, the oxidizing agent further comprises water.

In at least one embodiment, the composition comprises hydrogen peroxide. For example, the hydrogen peroxide may be used in an concentration ranging from 10 ppm to 60%, by weight relative to the total weight of the composition, for example from 1% to 60%, or from 1% to 50%, or from 1% to 40%, or from 1% to 30%, or from 1% to 20%, or from 1% to 10%, or from 5% to 10%, such as from 6% to 10%, by weight relative to the total weight of the composition.

Oxidation of performic acid source to performic acid can be catalyzed or non-catalyzed. For example, in some embodiments, the oxidation of the performic acid source can be catalyzed. In a further embodiment, the catalyzing comprises at least one of controlling the ratio of the performic acid source to the oxidizing agent in the composition, heating the composition, adjusting the pH of the composition, adding at least one catalyst to the composition, and/or irradiating the composition.

For example, the catalyzing may comprise controlling the ratio of the performic acid source to the oxidizing agent in the composition to be from 1:1000 to 1000:1 by volume, heating the composition, adjusting the pH of the composition to be from 0.1 to 8, adding at least one catalyst to the composition, or irradiating the composition.

In at least one embodiment, the catalyzing comprises controlling the ratio of the performic acid source to the oxidizing agent in the composition. In a further embodiment, the ratio of the performic acid source to the oxidizing agent in the composition may range from 1:1000 to 1:1000. For example, the ratio may range from 1:500 to 500:1, or from 1:200 to 200:1, or from 1:100 to 100:1, or from 1:50 to 50:1, or from 1:20 to 20:1, or from 1:10 to 10:1, such as from 1:8 to 8:1, or from 1:7 to 7:1, or from 1:6 to 6:1, or from 1:5 to 5:1, or from 1:4 to 4:1, or from 1:3 to 3:1, or from 1:2 to 2:1, or the ratio may be 1:1 on a molar basis. In some embodiments the ratio of performic acid source to oxidizing agent is at least 1000:1, is not more than 1000:1, is not more than 500:1, is not more than 200:1, is not more than 100:1, is not more than 50:1, is not more than 20:1, is not more than 10:1, is not more than 8:1, is not more than 7:1, is not more than 6:1, is not more than 5:1, is not more than 4:1, is not more than 3:1, is not more than 2:1, or is not more than 1:1 on a molar basis.

In some embodiments, the catalyzing comprises adjusting the pH of the composition, for example adjusting the pH of the composition to be from 0.1 to 8. In at least one embodiment, the catalyzing comprises adjusting the pH of the composition to be from 0.1 to 7, or from 0.1 to 5. In some embodiments the catalyzing comprises adjusting the pH of the composition to be from 0.1 to 3.

In at least one embodiment, the catalyzing comprises adding at least one catalyst to the composition. For example, the catalyst may comprise at least one of metal ions, acids, bases, or esters. The type and amount of catalyst can be chosen based on, for example, compatibility with other ingredients in the composition, the type and amount of residues, cost, the amount of energy or heat that would be generated in the reaction, and/or the degree of catalysis desired and additional functionalities.

For example, the catalyst may comprise at least one of metal, for instance a transition metal, such as, but not limited to, metal ions or metals from any of groups III to XII of the periodic table, and/or including transition metals, salts thereof and/or derivatives thereof, and/or metal oxides. For example, in some embodiments, the catalyst may be a metal ion, such as, but not limited to copper, zinc, nickel, iron, titanium, chromium, manganese, or silver.

In some embodiments, the catalyst may comprise acids, such as nitric acid; esters, or any other catalyst known in the art, for example, potassium, potassium permanganate, chromium, molybdenum, titanium and compounds or ions of phosphorous, iodine, sulfur, citrate, or ions or fine particles of lithium.

For instance, in some embodiments, the catalyst is a metal. For instance, the metal can be chosen from elements of groups III to XII of the periodic table, and/or can comprise metal ion(s). In some embodiments, the metal is chosen from copper, zinc, nickel, iron, manganese, titanium, and silver ions. In at least one embodiment, the catalyst comprises silver ions.

For example, the metal ions may be present in the composition in a concentration ranging from 1 ppb to 5 wt. %. For example, in some embodiments, the metal ions are present in a concentration ranging from 1 ppb to 2 wt. %, or from 1 ppm to 2 wt. %, or from 1 ppm to 1 wt. %, or from 1 ppm to 1000 ppm, or from 1 ppm to 100 ppm, or from 1 ppm to 50 ppm, or from 1 ppm to 10 ppm. The concentration of metal or metal ions can, for example, be chosen based on, e.g., degree of catalysis desired and/or suitability for the type of edible matter or substrate therefor, toxicity, environmental and other regulations and considerations, cost, other functions and/or the manner of application, and the like. For instance, the metal, in addition to its function as a catalyst, may provide enhanced or additional characteristics to the composition, such as disinfectant properties, including synergistic disinfectant properties when combined with an oxidant, bacteriostatic properties, and/or antimicrobial properties.

In some embodiments, the catalyzing comprises irradiating the composition. Irradiating the composition includes applying radiation from a natural source, such as the sun, or non-natural radiation source, such as UV or IR lamp. For example, the composition may be subjected to radiation, such as Ultraviolet (UV), infrared (IR) radiation, or visible radiation. In some embodiments the radiation is chosen from UV and IR radiation. In some embodiments, the radiation is both UV and IR radiation. Generally, UV radiation is radiation having a wavelength of less than 400 nm and IR radiation has a wavelength of greater than 700 nm.

Such radiation can be applied to the composition before or after treating the edible matter or substrate therefor and in any manner known to those of skill in the art. If UV and IR radiation are applied to a composition, they can be applied sequentially or at the same time and in any order.

In some embodiments, IR radiation having a wavelength ranging from 0.75 to 3.0 micrometers is applied to the composition. In further embodiments IR radiation having a wavelength of from 0.75 to 1.4 micrometers is applied. In another embodiment, a wavelength of from 1.4 to 3.0 micrometers is applied.

In some embodiments, UV radiation having a wavelength of less than 300 nm, such as less than 280 nm, or for example, less than 200 nm is applied to the composition. In at least one embodiment, the wavelength ranges from 200 nm to 10 nm.

In some embodiments, the temperature of the composition when applied to the edible matter is at or below room temperature. In other embodiments, the composition when applied to the edible matter is above room temperature.

In some embodiments, the temperature of the composition is elevated before or after applying the composition to edible matter or a substrate therefor.

According to various embodiments, the compositions can be effective over a wide range of temperatures. For example, in some embodiments, the composition remains stable at relatively high temperatures. A "stable" composition is a composition that has concentrations or amounts of active ingredients remaining, for example that have not undergone decay, sufficient to control, prevent or reduce qualitative losses, or to perform one or more of the functions described herein. In some embodiments, the composition is effective in the range of temperatures from 0° C. to 95° C. In some embodiments, the composition is effective in the range of temperatures from 20° C. to 95° C., such as from 35° C. to 95° C., or for instance from 35° C. to 95° C.

The stability of the composition can vary depending on the type and/or concentration of the performic acid source and/or oxidant in the composition, the temperature, other components in the composition or exposed to the composition, for example via the edible matter.

In some embodiments, the catalyzing comprises heating the composition. The composition can be heated in any manner suitable for heating the composition. For example, the composition may be heated by adding external radiant heat, applying the composition to heated edible matter, by applying a second heated composition to the composition, or by chemical reaction, such as supplying heat in the composition via an exothermic reaction.

In some embodiments, a method further comprises applying to the edible matter a second composition. For example, the second composition may have a temperature that is different, such as warmer, than the composition discussed hitherto, which in this paragraph and the next paragraph following will be referred to as the first composition. In some embodiments, the temperature of the second composition is at least 10° C. greater than the temperature of the first composition. In at least one embodiment, the temperature is at least 20° C. greater than the temperature of the first composition.

The second composition may provide other functions, for instance any of the functions disclosed herein, such as having disinfectant, herbicidal, insecticidal properties, etc. Accordingly, the components of the second composition will depend on the desired function and other considerations such as previously described for instance, toxicity, cost, environmental considerations, and the components in the first composition and/or the second composition and the type of edible matter or substrate.

In accordance with some embodiments, the second composition is substantially free of performic acid. The second composition may comprise any additive, oxidizing agent, or catalyst, such as those previously disclosed. For example, in some embodiments, the second composition comprises an oxidizing agent, such as hydrogen peroxide. In some embodiments, the second composition comprises at least one second acid.

The performic acid- or performic acid source-containing composition can be applied to the edible matter by any method suitable for applying the given composition to the edible matter or substrate therefor. For instance, depending the circumstances and the nature of the edible matter and/or the substrate therefor, the composition may be applied by spraying the composition on or near the edible matter, such as by hand spraying; by gassing the edible matter with the composition, such as by fogging, for instance dry fogging; by submerging, or dipping, the edible matter in the composition; or by injecting the composition into the edible matter. In some embodiments, the components of the composition may be applied as dry powders, liquids, gases, or any other readily available form. For instance, salicylic acid and/or hydrogen peroxide formulations may be applied to the edible matter or substrate in the form of a liquid, an aqueous solution or a dry solid, such as a powder. Edible matter and substrates therefor can be treated, according to certain embodiments, by providing the composition via irrigation water. In other words the irrigation water can serve as a vehicle for providing the composition to the edible matter or substrate.

In some embodiments, the composition is applied to edible matter or substrates therefor by fogging, such as dry fogging, or by providing a fine spray. As used herein, "dry fogging" means spraying droplets with particle sizes of less than and up to 1000 microns in diameter. For example, a dry fog may be produced by atomizing systems. In some embodiments, the composition is applied to the edible matter by dry fogging, wherein the dry fogging comprises applying the composition in the form of droplets of sizes less than or equal to 1000 microns onto the edible matter, such as less than 800 microns in diameter, or less than 100 microns, for instance, less than 10 microns, for example down to 0.001 microns.

A spray or fog can be formed by any suitable method based on the composition, edible matter or substrate, and/or the site conditions, physical constraints and so forth. For instance, a spray or fog may be formed by an ultrasonic sprayer or an ultrasonic microdroplet generator, for instance in an electronic method or a method wherein a vibrating disc creates resonance in a liquid, air-liquid sprayers, electric-ultrasonic foggers, cold foggers, hot foggers and the like.

In some embodiments, depending on the type of sprayer used, a dry fog optionally may be characterized by the air-to-liquid volume ratio. In at least some embodiments, the methods comprise applying a dry fog formed with an air liquid fogger, and in further embodiments, the fog has an air-to-liquid volume ratio ranging from 300:1 to 1200:1, for instance from 400:1 to 1000:1, or from 500:1 to 900:1, or from 500:1 to 800:1, or from 500:1 to 700:1.

The composition may be applied to edible matter or edible matter substrates intermittently, continuously, or in a single application.

The optimal concentrations and manner of applying can be determined, for example, based on the manner of applying the composition. For instance, in some embodiments, the composition may be diluted prior to application to prevent adverse deterioration or decay of the edible matter or substrate therefor as a result of the concentrations of components in the composition.

As used herein, "edible matter" includes, for example, foods, meat, plants, flowers, fruits, vegetables, tubers, bulbs, dairy products, grains, seeds, foliage, and drinking water. Edible matter is not limited by life-cycle stage, and thus includes for example seeds, bulbs, tubers, meats, plants, vegetables, flowers, foliage, fruits, grains, milk, dairy products, eggs and poultry, at all stages pre-planting or pre-conception through post-harvest or animal maturity, through sales, distribution, and consumption. In at least one embodiment, the edible matter is one of meat, plants, flowers, fruits, vegetables, tubers, bulbs, dairy products, and grains. In one embodiment, the edible matter is seeds.

For instance, edible matter includes cabbage, broccoli, cauliflower, kiwi, pear, pomegranate, eggplant, pepper, melon, carrot, tomato, garlic, persimmon, turnips, eggs, meat and/or animal carcasses, eggs and/or egg shells, milk, cheese, potatoes, sweet potatoes, citrus fruits, such as oranges, tangerines, grapefruits, onions and/or onion bulbs, flower bulbs, and the like.

Except where expressly stated otherwise, edible matter substrates include any substrate or vessel that may contact or be in proximity to the edible matter in the course of the life cycle of the edible matter, from pre-planting to post-harvest, through consumption and/or disposal of the edible matter. For instance, edible matter substrates include substrates, vessels, and materials used for storage and/or transport, such as boxes, crates, silos, box cars, vehicles; growth media, such as soil, soil substitutes, such as gels, coconut fibers, vermiculite, perlite; and processing facilities.

In at least one embodiment, the substrate is a growth medium. Many growth media may be suitable depending on the edible matter, including any materials that can grow or propagate a plant. Growth media can be natural or synthetic. According to certain embodiments, the growth medium is in solid form. Growth media include, for example, soil; vermiculite; perlite; clays, calcined clays, and clay pellets; coconut fibers, cocopeat, coir and coir peat; sand; diatomite; peat and peat-like mosses, such as hypnaceous moss, reed and sedge, humus or muck, and sphagnum moss; wood residues, such as leaf mold, saw dust, and barks; rice hulls; oasis cubes; bagasse; expanded polystyrene; urea formaldehydes; fiberglass; rockwool; gravel; lava rock; polymeric soil substitutes; soil amendments, such as nutrients for the soil, including for example substances comprising phosphoric acid and/or nitric acids, or minerals containing compositions, such as those providing micronutrients; and mixtures thereof. In at least one embodiment, the substrate is soil.

In some embodiments, the substrate is a storage container, such as for meat, plants, flowers, fruits, vegetables, tubers, bulbs, dairy products, grains, or soil.

Another aspect of the invention is a method of treating edible matter comprising obtaining a composition comprising performic acid in a concentration of at least 10 ppm, and applying the composition to the edible matter or a substrate therefor.

In some embodiments, the method comprises obtaining a composition comprising performic acid in a concentration ranging from 10 ppm to 85 wt. %, relative to the total weight of the composition, and applying the composition to the edible matter or a substrate therefor. For example, the composition may comprise performic acid in an amount ranging from 10 ppm to 50 wt. %, or from 10 ppm to 30 wt. %, or from 10 ppm to 20 wt. %, or from 10 ppm to 15 wt. %, or from 10 ppm to 13 wt. %, or from 10 ppm to 10 wt. %, or from 10 ppm to 7 wt. %, or from 10 ppm to 5 wt. %, or from 10 ppm to 4 wt. %, or from 10 ppm to 3 wt. %, or from 10 ppm to 2 wt. %, or from 10 ppm to 1.5 wt. %, or from 10 ppm to 1 wt. %, or from 10 ppm to 0.5 wt. %, relative to the total weight of the composition. The concentration of performic acid may depend on the concentration and types of oxidizing agents, catalysts in the composition, and the like, as well as the conditions for combining as disclosed above.

In some embodiments the composition comprising performic acid further comprises at least one of oxidizing agents, catalysts, and additives. For example, in one embodiment, the composition further comprises at least one oxidizing agent, such as those exemplary oxidizing agents disclosed herein. In some embodiments, the composition further comprises at least one catalyst, such as those exemplary catalysts disclosed herein. In at least one embodiment, the composition further comprises at least one additive, such as those exemplary additives disclosed herein.

The composition comprising performic acid may be in any form, such as a spray, a fog, a liquid, or a gas. For example, in some embodiments, the composition comprising performic acid is a gas, wherein the gas further comprises ozone.

Another aspect of the invention provides novel compositions. For example, the compositions comprise formic acid and performic acid and at least one additive. For example, the additive can comprise any of the components disclosed above, or in the examples below, and may be chosen, for example, based on the desired function, components of the composition, type of edible matter or substrate, manner of applying, and the like.

In some embodiments, the compositions comprising formic acid and performic acid further comprise at least one of an oxidizing agent, a catalyst and an additive. In at least one embodiment, the compositions can comprise at least one metal ion. In some embodiments, the at least one metal ion is at least one of a molybdenum ion, a chromium ion, a copper ion, a zinc ion, a nickel ion, an iron ion, a manganese ion, and a silver ion. In at least one embodiment, the composition comprises a silver ion.

Thus, it may be possible to optimize the treatment by manipulating either the time of treatment or the time of incubating the composition before applying the composition to the edible matter or to a substrate for edible matter. The conditions of such optimization may be selected based on, for example the type of edible matter or substrate, the composition, and/or the manner of applying.

Other embodiments of the invention will be apparent to those skilled in the art from consideration of the specification and practice of the invention disclosed herein. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Persons skilled in the art will also appreciate that by proper choice of the ingredients in the composition, it is possible to have a bactericidal or fungicidal composition that has essentially no gaps in its activity, i.e. it is a wide-spectrum anti-bacterial, anti-fungal, anti-microbial or the like with activity against nearly all strains of bacteria, fungi etc.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below. It is intended that the specification and examples be considered as exemplary only, with a true scope and spirit of the invention being indicated by the following claims.

EXAMPLES a. Preparation of Compositions

Compositions described in the following Examples 1-2 were prepared in the following manner; where multiple ranges or multiple values are listed for a given component, corresponding component amounts were used or contemplated for use over the course of the trial. Oxidizing agents were mixed in a first composition with any stabilizers, metal ions, or chelators. Next, in a second composition, acids were mixed with deionized water, and the pH was elevated to the target level with one or more bases. Next, in separate compositions, any solid/powder ingredients were dissolved to liquid stages. Finally, all the above compositions were slowly mixed to create a mixture comprising all the ingredients except the performic acid source.

The performic acid source was added to the mixture on-site, to generate the compositions comprising performic acid. The performic acid in the compositions was not stable, and the compositions were not active, for extended periods of time. That is, the performic acid concentration is not constant, as performic acid tends to decay to yield $CO_2$. When prepared at ambient or warm temperatures (50-60° C.) the compositions comprising performic acid were applied to the edible matter within 1-2 hours after combining performic acid with the mixture; application of the compositions under these conditions was also done immediately after mixing. At lower temperatures (below 20° C.), the composition comprising performic acid was more stable, and was applied from 5 hours to up to two months after combining the performic acid source with the mixture.

Example 1—Controlling Silver Scurf

The effect of compositions comprising performic acid on spore production of the silver scurf causal agent, *Helminthosporium solani*, on infected potato tubers was investigated. Silver scurf is widely considered to be a major source of quality loss in the fresh potato market. The four treatments for the study were: 1) 30 tubers were hand sprayed once with a 19:1 solution of tap water:performic acid composition ($H_2O_2$ 7 wt. %, 2 wt. % phosphonic acid, 1 wt. % phosphoric acid, HEDP (etidronic acid) 0.5 wt. %, glycerin 0.5 wt. %, silver 100 ppm, formic acid 3 wt. %, surfactant 0.1 wt. %, remainder distilled water, pH 2.8) (Table 2, treatment "A"); 2) 25 tubers were hand sprayed once with distilled water (Table 2, treatment "C"); 3) 25 tubers were hung in plastic mesh onion bags and fogged with the same formula of performic acid composition approximately once a month from December to March and twice a month from March to June (Table 2, treatment "B"); and 4) a fourth bag of tubers were kept in a separate cold storage room for the duration of the test (Table 2, treatment "D"). The performic acid composition in the fogging applications was as described below in Table 1.

TABLE 1

Silver Scurf Treatment Formulations

| | Fogging Formulation |
|---|---|
| Hydrogen peroxide (HP) | 5% to 10% |
| Phosphonic acid | 1% to 5% |
| pH regulators (caustic soda and/or ammonia) | to adjust pH to range 1 to 5 |
| Silver | 0, 50, 100, 250 or 500 ppm |
| Formic Acid | 1% to 7% |
| Alcohol | 0.5% to 3% |
| Benzoic Acid | 0.1% |
| Glycerin | 1% to 5% |
| HEDP | 0.5% to 2% |

Fogs were generated using ultrasonic foggers (compressed air combined with liquid, or electric ultrasonic foggers). The fogs were applied to potatoes at ratios of 200 cc to 1,000 cc per ton of potatoes at a holding temperature of from 7 to 9° C. at time periods of once per month to once every two weeks. Sprays were applied to potatoes at a volume of from 2 to 10 L per ton of potatoes with from 0.1% to 2% surfactant.

Hand sprayed tubers were laid out on a tarp in a single layer and the test solution or water was misted onto the tubers until glistening. The tubers were allowed to dry for 5 minutes, turned over, and the other half was sprayed until glistening. Tubers were allowed to dry for an additional 15 minutes and then placed into plastic mesh bags. Hand sprayed tubers were hung in a storage container and kept at 7.5 C and 92% room humidity (RH). The fogged tubers were placed in the same container. During each fog treatment in the container, the hand sprayed tubers were removed and kept in the dark at room temperature. The hand sprayed tubers where then returned to the container after all the fog had been exhausted from the container. Tubers treated with the fog were treated approximately nine times. After the last fog treatment tubers were washed and placed in plastic potato bags with holes. These bags were placed in potato boxes and incubated at 20° C. at 95% room humidity for 3 weeks. This temperature and humidity treatment is used to induce conidia production in *H. solani*. After incubation, the area of the tubers surface covered with *H. solani* spores was estimated by inspecting the tubers with a dissecting microscope. The results are summarized in Table 2 below.

TABLE 2

Number of Tubers with 0, 1, and 5% surface covered by *Helminthosporium solani* spores.

| | Silver Scurf Coverage | | |
|---|---|---|---|
| Treatment | 0% | 1% | 5% |
| A. Treated Hand Spray | 25 | 0 | 0 |
| B. Treated Fogged | 25 | 0 | 0 |
| C. Untreated Hand Spray | 18 | 11 | 1 |
| D. Untreated Controls | 24 | 3 | 2 |

As can be seen in Table 2, there were no *H. solani* spores observed on the surface of the 25 fogged or hand spray treated tubers. Of the 30 tubers hand sprayed with distilled water, eleven had 1% of their surface covered with spores, one had 5%, and 18 had no spores. Three of the untreated tubers kept in cold storage had 1% of their surface covered with spores, 2 had 5%, and 24 had no spores.

Example 2—Controlling Potato Sprouting

For part of a sprouting trial, compositions not comprising performic acid were applied to tubers (composition A), with tubers stored in a separate storage locker serving as an additional control. After several months, compositions comprising performic acid (composition B) were applied to the potatoes. The applied compositions were as described in Table 3.

TABLE 3

Sprouting Compositions

| | Composition A | Composition B |
|---|---|---|
| Hydrogen peroxide | 7% | 5% to 10% |
| Phosphonic acid | 3% | 1% to 5% |
| HEDP (HP stabilizer) | 1% | 0.5% to 2% |
| Silver | 50 ppm | 0, 50, 100, 250 or 500 ppm |
| Benzoic Acid | 0 | 0.1% |
| Surfactant | 0 | 0% to 2% |
| Sulfuric Acid | | 0.5% to 5% |
| Stabilizer (Solvay) | | about 1% |
| Glycerin | | 0.5% to 5% |
| Pure Formic Acid | 0 | 1% to 9% |
| D.I. water | qs. | qs |
| pH regulators (caustic soda and/or ammonia) | sufficient to raise pH | sufficient to raise pH |
| pH | 2.8 | 2.8 |

A fog was applied at ratios of from 200 cc to 1,000 cc per ton of potatoes with an ultrasonic fogger (compressed air plus liquid) at a holding temperature of 3 to 4° C. at time intervals ranging from once a month up to every two weeks from 14 Feb. 2010 to May 2010.

The compositions were also applied to the potatoes by direct spray with the compositions described, with and without formic acid and with and without phosphoric acid. In spraying applications, the compositions were diluted at a ratio of 1:9 with tap water and applied at a volume of 2-10 liters per 1 ton of potatoes with or without 0.1%-2% surfactant on the cleaning, sorting and packing line. The results are summarized in the following Tables 4 and 5.

TABLE 4

Treated Potatoes at 38° F.

| POTATO VARIETY | MEAN TUBER RATING* | | | | | | |
|---|---|---|---|---|---|---|---|
| | November 12 | December 1 | December 15 | December 29 | January 12 | February 23 | March 23 |
| W2310 | 0.9 | 0.9 | 1.5 | 1.8 | 2.1 | 2.2 | 2.1 |
| Blazer | 0.2 | 0.3 | 0.2 | 0.1 | 0.1 | 0.1 | 0.0 |
| Canela | 0.1 | 0.0 | 0.0 | 0.0 | 0.0 | 0.0 | 0.0 |
| Goldrush | 0.5 | 0.4 | 0.2 | 0.1 | 0.1 | 0.1 | 0.1 |
| Norkotah | 0.1 | 0.1 | 0.0 | 0.0 | 0.0 | 0.0 | 0.1 |
| Silverton | 1.1 | 1.1 | 1.0 | 1.0 | 0.7 | 0.5 | 0.2 |

*0 = no sprout;
1 = peeping to 1 mm;
2 = 1-5 mm;
3 = >5 mm

TABLE 5

Untreated potatoes stored at 55° F.

| POTATO VARIETY | MEAN TUBER RATING* | | | | | | | |
|---|---|---|---|---|---|---|---|---|
| | November 12 | December 1 | December 15 | December 29 | January 12 | January 26 | February 23 | March 23 |
| W2310 | 0.5 | 0.7 | 0.8 | 1.4 | 2.5 | 2.9 | 3.0 | |
| Blazer | 0.2 | 0.4 | 1.0 | 1.7 | 2.1 | 2.3 | 2.3 | 2.3 |
| Canela | 0.1 | 0.1 | 0.0 | 0.0 | 0.2 | 1.2 | 2.9 | 3.0 |
| Goldrush | 1.0 | 1.4 | 2.3 | 2.9 | 3.0 | 3.0 | 3.0 | |
| Norkotah | 0.1 | 0.0 | 0.1 | 0.3 | 1.0 | 2.4 | 3.0 | |
| Silverton | 1.8 | 2.0 | 2.3 | 2.8 | 2.9 | 2.9 | 3.0 | |

*0 = no sprout;
1 = peeping to 1 mm;
2 = 1-5 mm;
3 = >5 mm

As can be seen in above Table 5, all varieties of potatoes, other than Blazer, reached an unacceptable rating of 3 by February 23 without treatment. In contrast, the treated samples (Table 4) suppressed sprouts in all varieties with the addition of a peroxide treatment (composition A), and then kept the same or better score following subsequent treatments with the inventive composition (composition B). For example, the W2310 and Silverton varieties unexpectedly showed a lower score following the formic acid treatment, indicating a reduction in the sprouting of the tubers.

Example 3—Citrus Treatment

The effect of performic acid compositions was studied on citrus fruit. To prevent decay in citrus during storage, generally, people have applied fungicides, such as Imazalil and thiabendazole, during packaging and waxing to treat the citrus fruit. However, as fungicides can be toxic, many countries have instituted limits on the levels of such agents in edible matter. For example, the U.S. limits the level of Imazalil to 10 ppm. There is a need for reducing the levels of potentially toxic substances in citrus and/or replacing such materials with environmentally friendly and safe products.

Approximately 1000 mandarin oranges were treated shortly after harvest with compositions comprising performic acid, water, or an Imazalil composition, and then stored at 2° C. After 22 days, the number of rotten fruits, and the percent decay were assessed. A second trial was conducted with ten tons of mandarin oranges treated with a performic acid composition or Imazalil and stored and then stored at 2° C. The study was repeated with Red Grapefruit. The compositions comprising performic acid and the manner of applying the compositions varied throughout the course of the study within the parameters summarized in Table 6.

TABLE 6

Performic Acid Composition

| | |
|---|---|
| Hydrogen peroxide | 2% to 20%* |
| Phosphonic acid | 1% to 10%** |
| pH regulators (caustic soda and/or ammonia) | to raise pH to range of 1 to 5 |
| Surfactant | 1% to 2%*** |
| formic acid | 1% to 15%**** |
| Silver | 0 ppm, 50 ppm or 100 ppm |

*depending on state of contamination: 4% to 8% for low state of contamination
**depending on state of contamination: 1% to 5% for low state of contamination
***depending on state of contamination: 0.1% to 1% for low state of contamination
****depending on state of contamination: 1% to 5% for low state of contamination The compositions were applied to the citrus at room temperature with a fine spray of the performic acid containing composition and then treated either a) with a drain wash of water (either cold or heated to 55° C.) with a 1:9 dilution in tap water of the composition without formic acid, or b) with a drain wash of water (either cold or heated to 55° C.), followed by a fine spray at room temperature with a formulation identical to the performic acid formulation but without formic acid. Thus, the methods of applying in this study were:

a. Application of the performic acid containing composition at room temperature with fine spray, then treatment with a drain wash of cold water, and then a fine spray at room temperature with a formula without formic acid (i.e. without the performic acid source)

b. Application of the performic acid containing composition at room temperature with fine spray, then treatment with a drain wash of heated water (to about 55° C.), and then a fine spray at room temperature with a formula without formic acid
c. Application of the performic acid containing composition at room temperature with fine spray and then treatment with a drain wash of cold water that contained the formula at a diluted state at a ratio of 1:9 but without formic acid
d. Application of the performic acid containing composition at room temperature with fine spray and then treatment with a drain wash of heated water (to about 55° C.) that contained the formula at a diluted state at a ratio of 1:9 but without formic acid All treatments were conducted at a total rate of 5-20 liter of formula per ton of different Citrus varieties. The results are summarized in Table 7, below.

TABLE 7

Treated Citrus Fruit

| Fruit | Days after treatment | Treatment | No. Treated Fruits | No. Rotten Fruits | % Decay |
|---|---|---|---|---|---|
| Mandarin Orange | 22 | Water | 1008 | 32 | 3.17 |
| | | Imazalil | 864 | 59 | 6.8 |
| | | Performic acid composition | 1008 | 7 | 0.6 |
| Mandarin Orange | 46 | Imazalil | 7140 | 125 | 1.75 |
| | | Performic acid composition | 7140 | 109 | 1.51 |
| Red Grapefruit | 35 | Water | 3575 | 167 | 4.67 |
| | | Performic acid composition | 3575 | 41 | 1.14 |

As can be seen in the above Table 7, the inventive method resulted in a lower level of decay in both mandarin oranges and Red Grapefruit, with reduced levels of chemical residue, in comparison to the prior art fungicidal treatment or water treatment.

Example 4—Seed Treatment

Several compositions were prepared, as described in Table 8 below (percentages are given in weight percent), and applied to seeds.

TABLE 8

Seed Treatment Compositions

| | Composition | | | | | | | | | |
|---|---|---|---|---|---|---|---|---|---|---|
| Ingredients | Control | 9 | 8 | 7 | 6 | 5 | 4 | 3 | 2 | 1 |
| $H_2O_2$(%) | 10 | 10 | 10 | 10 | 5 | 10 | 10 | 10 | 10 | 10 |
| $H_3PO_3$(%) | 3 | 1 | 1 | 3 | 1 | 1 | 1.5 | 1.5 | 2 | 3 |
| $(COOH)_2$ (%) | | | | | 1 | 1 | | 1.5 | | |
| HCOOH (%) | | | 3 | 3 | | 1 | 1 | 1.5 | | |
| $H_3BO_3$(%) | | | | 1 | | | | | | |
| $ZnSO_4$(%) | | | | | 0.01 | | | | | |
| $CUSO_4$ (%) | | | | | | | | 0.01 | | |
| Ag (ppm) | 250 | 250 | 250 | 250 | 250 | 250 | 250 | 250 | 500 | 250 |
| Benzoic Acid(%) | | | | | | | | | 0.10 | |
| Sorbic Acid (%) | | | | | | | | | 0.10 | |
| Glycerin(%) | 2 | | | 2 | | | | | 2 | 2 |
| HEDP(%) | | 0.5 | 0.5 | 0.5 | 1 | 1 | 1 | 1 | 1 | 0.5 |
| Alcohol (%) | | | | | | | | | 2 | |
| Surfactants | 0.10 | | | + | + | | | | | |

Example 5—Testing Stability of Hydrogen Peroxide Solutions in Soil Treatment 100 g of Loess soil from a potato field in the Negev were mixed with 40 ml water, 10.7 g $H_2O_2$ and Bayhibit® AM (2-phosphonobutane-1,2,4-tricarboxylic acid, up to 0.5% of the final solution) from a European source. The solution was checked as-is and the $H_2O_2$ concentration in the solution (before mixing with the soil) was 7.1%. The theoretical concentration of hydrogen peroxide in the mixture with the soil was 0.5% $H_2O_2$. Another sample was taken after 60 seconds of mixing with the soil and the $H_2O_2$ concentration was 1.1%; apparently the solution was not homogeneous, as there was effervescence in the solution. After 15 minutes the $H_2O_2$ concentration in the mixture was 0.51%, after 30 minutes the $H_2O_2$ concentration was 0.4% and after 60 minutes the $H_2O_2$ concentration was 0.19%. This procedure was repeated and parallel titrations of the $H_2O_2$ concentration were conducted; identical results were obtained.

The procedure was repeated again, again using 100 g Negev Loess soil, 40 ml water, 10.7 g $H_2O_2$ solution with HEDP (etidronic acid) from a Chinese supplier. The theoretical concentration of $H_2O_2$ in the new mixture was 0.5%. The specific weight of the mixture was about 1.2. After 60 seconds of stirring the concentration of hydrogen peroxide was 0.661% (apparently the solution is not homogenous), after 15 minutes the $H_2O_2$ concentration was 0.510%, after 30 minutes the $H_2O_2$ concentration was 0.357%, after 60 minutes the $H_2O_2$ concentration was 0.2%. The solution was then left overnight without stirring; the $H_2O_2$ concentration in the morning was 0.02%.

Example 6: Stability of Phosphonic Acid in Contact with Hydrogen Peroxide 250 ml solutions were prepared, each containing 10% $H_2O_2$ and 10% phosphonic acid; these were kept in an incubator at 55° C. and at room temperature

| | $H_2O_2$ concentration, wt. % | |
|---|---|---|
| Time | at room temperature | at 55° C. |
| 0 minutes | 11.1% | 11.1% |
| 15 minutes | 11.1% | 10.9% |

-continued

| Time | $H_2O_2$ concentration, wt. % | |
|---|---|---|
| | at room temperature | at 55° C. |
| 30 minutes | | 10.7% |
| 60 minutes | 11.0% | 10.7% |
| 120 minutes | 11.0% | 10.9% |
| 240 minutes | | 10.6% |
| 360 minutes | 10.8% | 10.7% |
| 24 hours | 10.8% | 9.9% |
| 48 hours | 10.3% | 9.9% |
| 168 hours | 10.3% | 6.4% |

Example 7—Stability

A concentrated aqueous 20% $H_2O_2$ solution was prepared containing $H_2O_2$ 20%, phosphonic acid 8.0%, phosphoric acid 2.0%, glycerin 6.0%, silver 300 ppm. The $H_2O_2$ concentration was checked: 20.1%. A portion of the solution was placed in an incubator at 55° C. and a portion was stored at room temperature. To 95.5 g of the solution at 55° C. were added 4.5 grams of HEDP from a European supplier. The solution was checked for the $H_2O_2$ concentration therein:

| Day of test | Concentration of $H_2O_2$ % at 55° C. without HEDP | Concentration of $H_2O_2$ % at 55° C. with HEDP | Concentration of $H_2O_2$ % at room temperature without HEDP |
|---|---|---|---|
| 1 | 20.1 | 16.8 | 21.0 |
| 2 | 17.9 | 15.0 | 20.9 |
| 7 | 4.0 | 6.5 | 19.2 |
| 8 | 3.4 | 5.1 | 18.2 |

Example 7—Citrus Treatment Compositions

While mixing with a mixer were added, in order, 75 g phosphonic acid; 700 g distilled water; approximately 83.5 g 47% sodium hydroxide carefully and slowly while mixing until a pH of 2.7 was reached (this resulted in an exothermic reaction which heated the solution); 10 g active material (STEPFAC 8182, a phosphate ester of an alkyl polyethoxyethanol that acts as a wetting agent); the solution was allowed to cool almost to room temperature; to the cooled solution were added 100 g 50% hydrogen peroxide into which had been mixed 5.7 g of 100 ppm silver solution; distilled water (approximately 13 g) was added to top off the amount to 987 g.

At this point 500 g of the solution were poured off to a bottle to be used in the "hot" solution. The night before the experiment, 12.5 g formic acid were added to the remaining 487 g of solution to obtain 500 g of mixture to be used to prepare a "cold" solution.

To prepare the "cold" solution; 4.5 liters of tap water at room temperature were mixed with the 0.5 liter solution; to prepare the "hot" solution, 4.5 liters of water at 56° C. were mixed with the 0.5 liter solution.

Example 8—Treatment of Citrus

Five liters for use in a cold liquid wash were prepared, containing 0.1% silver solution (equivalent to 100 ppm silver), 7.5 wt. % phosphonic acid, 5 wt. % hydrogen peroxide, 0.1 wt. % alkyl glycoside surfactant, 2.5 wt. % formic acid, and the remainder water; the solution was prepared by mixing the ingredients in the order listed.

Similarly, 5 liters for use in a hot liquid were prepared, containing 0.1% silver solution (equivalent to 100 ppm silver), 7.5 wt. % phosphonic acid, 5.0 wt. % hydrogen peroxide, 0.1 wt. % alkyl glycoside surfactant, and the remainder water; the solution was prepared by mixing the ingredients in the order listed.

Prior to use, each of the two 5 liter solutions was diluted in 20 liters of tap water; a white precipitate formed.

The efficacy of the solution was tested as follows: 150 kg of mandarins were divided into mesh bags and then sequentially submerged and shaken in the cold liquid so that each bag had the same contact time with cold liquid (about 60-90 seconds from initial immersion until the bag reached the next station in the production line). Next, each bag was submerged for about 30 seconds at 50° C. in the hot solution. The bags with the mandarins were then placed in a large container, from which they were transferred to the production line. At the next station they were passed through a dehydration cell, in which they were blown with hot air, after which they were waxed, hand sorted and packed in 10 cartons of 16 kg each. They were then palleted with an untreated control group and placed in cold storage (about 4±2° C.) for 3 weeks. The results in terms of percentage of rotten fruits (17 fruits out of 60 boxes, each box containing about 120 fruits) was about the same (21 fruits out of 60 boxes) as the old commercial process already in use on that particular production line for limiting rotting.

Example 9

The goal was to form 20 liters of concentrated solution with the addition of a surfactant and to compare the activity of this surfactant-containing material to the activity of material without a surfactant. To a 1% phosphonic acid solution was added silver to a concentration of 2 ppm. A solution of 50% NaOH was mixed in until the pH of the solution was 3.8. A portion of this was separated and to that portion was mixed in an alkyl glycoside surfactant to a concentration of 0.1%. To compare the effects of the two solutions, 3 sweet potatoes were sprayed 7 times at intervals of 15-20 minutes with the non-surfactant solution and 3 sweet potatoes were sprayed 7 times with surfactant-containing solution; the vegetables were sprayed until dripping, then allowed to dry before being sprayed again. The effect of spraying was checked afterward; the treatment significantly improved shelf life and appearance. It was noted that there was a problem with foaming in the nozzles of the sprayer.

Example 10

The goal of this experiment was to prepare 1.5 liters of a solution containing 0.1% silver, 7.5% phosphonic acid and 5.0% hydrogen peroxide; the solution could then be 5-fold diluted prior to use. Into 1155 g of water were mixed 112.5 g phosphonic acid; the pH value of the solution at this stage was 1.2. The pH value was raised to 2.5 by addition of 50 ml of 50% sodium hydroxide solution with mixing. This was an exothermic process. Into the resulting hot solution was added 7.5 g surfactant (alkyl polyglycoside), mixed until fully dissolved. After allowing to cool, to the solution were added 150 g of 50% $H_2O_2$ in which was dissolved 8.6 g stabilizer-containing silver solution. This yielded approximately 1500 ml of solution, which was divided into two bottles of 750 ml each. To one of the bottles were added 18.75 g of formic acid. The $H_2O_2$ concentration before addition of formic acid was 5.3%, and after addition of formic acid, after 24 hours at room temperature, the $H_2O_2$ concentration was 5.1% (theoretically 5.15% after addition of formic acid).

Example 11—Solutions for Treatment of Sweet Potatoes

An aqueous solution containing 1 wt. % phosphonic acid, 0.5 wt. % or 0.25 wt. % glycerin, and 0.5 wt. % formic acid was prepared and sprayed seven times on sweet potatoes. In comparison to untreated controls, the sweet potatoes obtained had a longer shelf life and an improved appearance.

Example 12—Solutions for Arresting Sprouting of Potatoes Post-Harvest

The following table list amounts of ingredients to be mixed to prepare one liter of solution

|  | Sol'n 1 | Sol'n 2 | Sol'n 3 | Sol'n 4 | Sol'n 4A |
|---|---|---|---|---|---|
| $H_2O_2$ 50% solution | 116 g | 116 g | 116 g | 116 g | 116 g |
| $H_3PO_3$, 95% solution | 30 g | 30 g | 30 g | 30 g | 30 g |
| Silver Sol'n (Stabiliser), 100 ppm | 0.57 g | 0.57 g | 0.57 g | 0.57 g | 0.57 g |
| HEDP, 50% sol'n | 8.3 g | 8.3 g | 8.3 g |  | 8.3 g |
| Benzoic Acid | 1.2 g | 1.2 g | 1.2 g | 1.2 g |  |
| Surfactant, 100% sol'n |  | 1 g | 1 g | 1 g |  |
| $H_2SO_4$, 98% sol'n |  |  | 10 g | 10 g | 10 g |
| Glycerin 100% | 5 g | 5 g | 5 g | 5 g | 5 g |
| $H_2O$ | 788.9 g | 788 g | 778 g | 786.2 g | 778 g |
| Formic acid, 95% sol'n | 50 g | 50 g | 50 g | 50 g | 50 g |

Solutions 1 and 3 were prepared. The solutions were prepared without raising the pH and without formic acid; before use it is necessary to add to each bottle 40 ml (50 g) of 95% formic acid.

Solution 1: $H_2O_2$ concentration before addition of formic acid was 7.4%, pH was not raised. Solution 2: not prepared. Solution 3: $H_2O_2$ concentration before addition of formic acid was 7.3%, benzoic acid was not added (doesn't dissolve in the solution), surfactant (alkyl polyglycoside) was added, the pH was not raised.

Solution 4: formic acid was added immediately during preparation, pH was not raised, surfactant was not added, $H_2O_2$ concentration immediately after addition of formic acid was 7.03%. The solution was transferred to a closed bottle and the rate of performic acid formation checked. After 90 minutes the solution in the bottle was checked, the bottle expanded slightly, and the $H_2O_2$ concentration was 6.6%, i.e. a 5.7% drop in concentration. $H_2O_2$ concentration was still 6.6% after four days.

Solutions 1 and 4 were sprayed on young potatoes. Results versus control: with solution 1, potatoes gained a brown tint (it should be noted that solution 1 was sprayed as-is without dilution with formic acid, i.e. the $H_2O_2$ concentration was 7.4%). With solution 4, the tint of the potatoes was browner than the control but less brown than with solution 1 (note that the concentration of the $H_2O_2$ at the time of spraying was 6.6%).

After 3 days on the potatoes that were sprayed with the aforementioned solutions there was observed a blackening of the sprouts, in parallel these potato skins appeared as if they had undergone glazing. Since the goal was to find a concentration that would cause the aforementioned blackening but not glaze the skin, to 200 g of solution 4 were added 1.5 g glycerin and 48.5 g water.

Solution no. 5 was prepared containing 5.56% $H_2O_2$, 2.4% phosphoric acid, 100 ppm silver, 0.8% sulfuric acid, 4.0% formic acid, and water to complete to 100%. Phytotoxic injuries were observed on the potatoes that were sprayed with solution 5. Solution 5 was diluted two-fold to yield solution 5A; solution 5A was diluted two-fold to yield solution 5B. These solutions were sprayed on potatoes.

Solution 6 was prepared; this is like solution 4 but the $H_2O_2$/formic acid ratio was 1:1 and not like solutions 4, 5 and their derivatives, in which the ratio was is 3:7. Solution 6: 50 g 3.0% $H_2O_2$, 30 g 3.0% phosphoric acid, 0.57 g 100 ppm silver, 10 g 1.0% sulfuric acid, 30 g 3.0% formic acid, 880 g water to fill to 100%. The solution was left for 60 minutes after preparation and afterward sprayed on potatoes. Phytotoxic injuries were observed on potatoes, but these were attributed to the variety of potato used (Vivaldi) which is an incomplete skin variety in which skin injuries are known to occur. The experiment was discontinued.

Example 13—Preparation of Various Formulations

In this example, the ingredients were mixed in the order recited; in cases in which hydroxide was added to an acidic mixture to raise the pH, this resulted in an exothermic reaction which raised the temperature of mixture.

SpuDefender Classic (preparation of 2000 g): 60% hydrogen peroxide, 223 g (7% in the final preparation); 85% phosphoric acid, 82.3 g (3.5% in the final preparation); silver solution, 1.6 g (140 ppm silver in the final preparation); remainder distilled water (1683.1 g)

Classic+F SpuDefender (preparation of 2000 g): 60% hydrogen peroxide, 223 g; 85% phosphoric acid, 82.3 g; silver solution, 1.6 g (140 ppm in the final preparation); 60 g formic acid (3.0% in the final preparation); remainder distilled water (1623.1 g).

Classic+F/2 SpuDefender: after waiting 2 hours to allow formation of performic acid in the Classic+F SpuDefender solution, this solution was diluted to half strength by addition of an appropriate amount of water to yield the title solution.

SpuDefender Natural (preparation of 2000 g): 60% hydrogen peroxide, 223 g; formic acid, 60 g (3.0% in the final solution); remainder distilled water (1705.4 g).

SpuDefender Natural/2: after waiting 2 hours to allow formation of performic acid in the SpuDefender Natural solution, this solution was diluted to half strength by addition of an appropriate amount of water to yield the title solution.

SpuDefender Joker: this was prepared like the Classic SpuDefender solution, except the concentration of phosphoric acid in the final preparation was 7.5%.

SpuDefender Joker+F: this was like the Classic+F SpuDefender solution, except the concentration of phosphoric acid in the final preparation was 7.5%; it was prepared by mixing 45 g formic acid into 1455 g SpuDefender Joker.

Example 14—SeedGuard Solutions

Preparation of SOL1+ Solution:

| SOL1+ | SOL5 | SOL4 | SOL3 | SOL2 | SOL1 | Ingredients |
|---|---|---|---|---|---|---|
| % | This is a solution which was bought from Solvay | % | % | % | % | |
| 7 | | 7 | 7 | 7 | 7 | H2O2 |
| | | 3 | | | | H3PO3 |
| 5 | | — | 3 | 3 | 5 | H3PO4 |
| 100 ppm | | 100 ppm | 100 ppm | 100 ppm | 100 ppm | Ag |
| None | | None | None | 1 | None | H2SO4 |
| 0.5 | | 0.5 | 0.5 | 0.5 | 0.5 | HEDP |
| 0.1 | | 0.1 | 0.1 | None | None | Surfactant |
| 0.5 | | 0.5 | 0.5 | 0.5 | 0.5 | Glycerin |
| None | | 3 | 3 | 3 | None | Formic acid |
| pH 2.8 | | pH 2.8 | pH 2.8 | | | |

Performic acid-containing solutions: A working solution of 3 liters at pH 2.8 having the following concentrations was prepared: 2% phosphonic acid, 2.0% BLS, 0.5% Glycerin, 0.1% alkyl polyglycoside.

A concentrated solution of 1 liter was prepared containing 20% phosphonic acid; the solution should be diluted with 9 parts water to obtain a 2% phosphonic acid solution or with 19 parts water to obtain a 1% phosphonic acid solution. In addition to 20% phosphonic acid, the concentrated solution should contain 20% BLS, 2% $H_2O_2$, 5.0% glycerin, and 1.0% surfactant at pH 2.8.

Example 15—Solutions for Arresting Sprouting

Volume of each solution was 500 ml. The following were prepared: (1) SpuDefender: 5% $H_3PO_3$; 5% $H_3PO_4$; 5% formic acid; 7% $H_2O_2$+5% formic acid; 4% $H_2O_2$+4% $H_3PO_4$; (2) ½N SpuDefender; 2.5% $H_3PO_3$; 2.5% $H_3PO_4$; 2.5% formic acid; 5% $H_2O_2$+3% formic acid; 3% $H_2O_2$+4% $H_3PO_4$; (3) ½N Solvay solution 4+formic acid; (5) control with water; (6) control without water.

An experiment was conducted using the following formulation: 7.0% hydrogen peroxide, 100 ppm of 17% silver solution, 1.0% sulfuric acid, 0.5% glycerin, 5.0% formic acid. The formulation was applied to table potatoes of different varieties: Lady Rosetta, Morris Pfeifer, Nicola.

Example 16—SeedGuard Solution

| SOL2+ % | Ingredients |
|---|---|
| 7 | H2O2 |
| | H3PO3 |
| | H3PO4 |
| 100 ppm | Ag |
| 1 | H2SO4 |
| 0.5 | HEDP |
| None | Surfactant |
| 0.5 | Glycerin |
| 5 | Formic Acid |

In order to obtain a solution that would not be phytotoxic, this solution did not contain phosphonic or phosphoric acids, and the concentration of formic acid was increased from 3% to 5%. The formulation was applied by spraying (hand spray till dripping) to table potatoes of various varieties: Lady Rosetta, Morris Pfeifer, Nicola. Five days after application and storage at room temperature, the potatoes were checked. There was slight phytotoxicity in places on the potatoes where the applied formulation didn't dry (for example due to contact with other surfaces), but as desired there was blackening, shrinking and drying of the sprouts. In one of the potatoes of the Nicola variety new white pips were observed.

Example 17

The following solutions, which according to results obtained were most effective, were prepared again:

| SOL4 Solvay | SOL5 % | SOL2/2B | SOL2/2 % | Ingredients |
|---|---|---|---|---|
| 7 | 7 | 5 | 5 | $H_2O_2$ |
| 3 | 3 | | | $H_3PO_3$ |
| | | | | $H_3PO_4$ |
| 100 ppm | 100 ppm | 100 ppm | 100 ppm | Ag |
| 1 | None | 0.5 | 0.5 | $H_2SO_4$ |
| Solvay's | 0.5 | 0.5 | 0.5 | HEDP |
| Solvay's | 0.1 | None | None | Surfactant |
| 0.5 | 0.5 | None | 0.5 | Glycerin |
| 3 | 3 | 3 | 3 | Formic Acid |
| pH 2.8 | pH 2.8 | | | |
| 0.10 | | | | Benzoic acid |

Sol2/2 Solution: contains formic acid, dilutions were made on-site shortly before use. SOL2B/2B solution contains formic acid but not glycerin, dilutions were made on-site shortly before use. SOL5 solution contains formic acid, dilutions were made on-site shortly before use. SOL4 solution: contains formic acid, dilutions were made on-site shortly before use; there were only 270 grams of solution.

Example 18—Solutions for Disinfecting Potatoes Before Placing them in Storage Rooms A solution containing (after dilution) phosphonic acid 0.8%, $H_2O_2$ 1%, silver 15 ppm, formic acid 0.5% was prepared. In order to prepare the solution before dilution, to 4.8 liters of concentrated solution were added 0.2 liters of formic acid. Formulation for concentrated solution: phosphonic acid 8%, NaOH 100% (solid): approximately 4%; 50% $H_2O_2$, 20%; silver 150 ppm; formic acid: 5%; alkyl polyglycoside 0.2%, remainder distilled water to 100%

Solution 1: 25 kg were prepared as follows: phosphonic acid, 2.68 kg of 70% solution; NaOH 47%, 2.0 kg; $H_2O_2$ 50%, 2.5 kg; 17% silver solution 0.015 kg; 85% formic acid, 0.625 kg; alkyl polyglycoside 0.04 kg; distilled water 17.175 kg. Following this, 1.5 parts solution were diluted with 8.5 parts water. Concentration of materials after dilution: phosphonic acid: 1.12%, $H_2O_2$ 0.75%, silver 16 ppm, formic acid 0.375%. In order to prepare the solution before dilution, to 3.0 kg of concentrated solution were added 75 g of formic acid.

Solution 2: 25 kg were prepared as follows: phosphonic acid, 2.15 kg of 70% solution; NaOH 47%, 1.5 kg; $H_2O_2$ 50%, 7.5 kg; 17% silver solution, 0.02 kg; 85% formic acid, 1.65 kg; distilled water 11.64 kg. Following this, 1 part solution was diluted with 9 parts water. Concentration of materials after dilution: phosphonic acid, 0.602%; $H_2O_2$, 1.5%; silver, 14 ppm; formic acid: 0.66%. In order to prepare the solution before dilution, to 2 kg of concentrated solution 141.3 g of formic acid were added.

Example 19—SeedGuard Solution for Treatment at Azata

For preparing 25 kg of solution 1:

| Amount for 25 kg kg | SOL5 % | Ingredient |
|---|---|---|
| 3.5 (50% solution) | 7 | $H_2O_2$ |
| 1.071 (70% solution) | 3 | $H_3PO_3$ |
| 0.0143 | 100 ppm | Ag |
| 0.208 (60% solution) | 0.5 | HEDP |
| 0.02 | 0.08 | Surfactant |
| 0.125 | 0.5 | Glycerin |
| 0.250 | | $H_2SO_4$ |
| 0.400 (100% analytical solution) | 1.6 | NaOH |
| 0.750 (85% solution) | 3 | Formic Acid |
| 18.48 | To 100 pH 2.8 | Aqua Dis |

Stable Performic Acid Formulations

Also provided in accordance with embodiments of the invention are stable formulations of performic acid. While such formulations, like the performic acid-containing formulations described in the examples above, may be formulated on-site just prior to use, for example by adding one of the reactive ingredients (e.g. $H_2O_2$, ozone, or formic acid) shortly before use, in some embodiments of the present invention the formulations may be formulated off-site and stored, without significant loss of performic acid during storage. Such stable formulations may be made in concentrated form, so that an end user may dilute the formulation with tap water, for example in ratio of concentrated formulation:water of 1:1, 1:2, 1:5, 1:10, 1:20, 1:30, 1:50, 1:70, 1:100, 1:120, 1:150, 1:200, 1:250, 1:300, 1:350, 1:400, 1:450, or 1:500, to obtain a working solution on-site. In addition, there are provided in accordance with embodiments of the invention pre-mixes to which one of the reactive ingredients may be added on-site to make the performic acid just prior to use. The following examples illustrate some such stable performic acid-containing compositions.

Example 20

A composition was prepared containing $H_2O_2$, phosphonic acid which had been partly neutralized with KOH, formic acid, citric acid, and one or more alkyl polyglycoside surfactants; as will be appreciated by persons skilled in the art, performic acid is formed in situ. It was found that stable, concentrated solutions, which may later be diluted on-site just prior to use, may be formed when the concentration of $H_2O_2$ (or other oxidizer, e.g. ozone) in the mixture is approximately 15 wt. %, and the concentration of formic acid is approximately 10-12 wt. %; these figures reflect the weight percentages upon completion of the mixture, before performic acid formation has proceeded appreciably, as the percentages of both $H_2O_2$ (or other oxidizer) and formic acid in the mixture drop from their initial values as performic acid formation proceeds. Of course, if it is desired to make a less concentrated solution, e.g. by forming the performic acid on-site using already diluted ingredients, the weight percentages of the ingredients may be significantly lower. Also, while herein formic acid has been used as the performic acid source, it will be appreciated that other compounds or mixtures of other compounds may serve as performic acid sources, as has been described above.

Regarding the concentrations of the ingredients prior to addition to the mixture, these concentrations may be as follows:

$H_2O_2$: in some embodiments the concentration of $H_2O_2$, prior to addition to the mixture in which performic acid is formed, is at least 0.1% by weight. In some embodiments the concentration is at least 0.2 wt. %. In some embodiments the concentration is at least 0.25 wt. %. In some embodiments the concentration is at least 0.3 wt. %. In some embodiments the concentration does not exceed 70 wt. %. In some embodiments the concentration does not exceed 50 wt. %. In some embodiments the concentration does not exceed 35 wt. %. In some embodiments the concentration does not exceed 20 wt. %. In some embodiments the $H_2O_2$ concentration, prior to addition to the mixture in which performic acid is formed, is from 0.1 wt. %-70 wt. %. In some embodiments the $H_2O_2$ concentration is from 0. wt. 2%-50 wt. %. In some embodiments the $H_2O_2$ concentration is from 0.25-35 wt. %. In some embodiments the $H_2O_2$ concentration is from 0.3-20 wt. %. In some embodiments the $H_2O_2$ concentration is from 3%-15 wt. %. It will also be appreciated that when other compounds are used as oxidizers they may included in concentrations similar to those listed above.

Formic acid, when used: in some embodiments, the formic acid concentration is at least 3 wt. %. In some embodiments, the formic acid concentration is at least 5 wt. %. some embodiments, the formic acid concentration is at least 10 wt. %. In some embodiments, the formic acid concentration is not more than 70 wt. %. In some embodiments, the formic acid concentration is not more than 50 wt. %. In some embodiments, the formic acid concentration is not more than 35 wt. %. In some embodiments, the formic acid concentration is not more than 25 wt. %. Also, when formic acid is used, it has been found that using a 1:1 ratio of formic acid to hydrogen peroxide gives very stable results.

Phosphonic acid, partly neutralized: in some embodiments, the phosphonic acid is partly neutralized before its addition to the mixture in which the performic acid is formed. In some embodiments, the partial neutralization is carried out using KOH. In some embodiments, the phosphonic acid is partly neutralized to a pH of not less than 1. In some embodiments, the phosphonic acid is partly neutralized to a pH of not less than 1.5. In some embodiments, the phosphonic acid is partly neutralized to a pH of not less than 1.7. In some embodiments, the phosphonic acid is partly neutralized to a pH of not less than 2. In some embodiments, the phosphonic acid is partly neutralized to a pH of not less than 2.5. In some embodiments, the phosphonic acid is partly neutralized to a pH of not less than 3. In some embodiments, the phosphonic acid is partly neutralized to a pH of not less than 3.5. In some embodiments, the phosphonic acid is partly neutralized to a pH of not more than 10. In some embodiments, the phosphonic acid is partly neutralized to a pH of not more than 9. In some embodiments, the phosphonic acid is partly neutralized to a pH of not more than 7. In some embodiments, the phosphonic acid is partly neutralized to a pH of not more than 5. In some embodiments, the phosphonic acid is partly neutralized to a pH of not more than 4.5. In some embodiments, the phosphonic acid is partly neutralized to a pH of not more than 4.0. In some embodiments, the phosphonic acid is first partly neutralized to a pH of 1-10. In some embodiments, the phosphonic acid is partly neutralized to a pH 1.1-9. In some embodiments, the phosphonic acid is partly neutralized to a pH of 1.2-7. In some embodiments, the phosphonic acid is partly neutralized to a pH 1.5-5. In some embodiments, the phosphonic acid is partly neutralized to a pH of 2-4.5. In some embodiments, the concentration of the phosphonic acid, prior to addition to the mixture in which performic acid is formed, is at least 0.1 wt. %. In some embodiments, the concentration is at least 0.2 wt. %. In some embodiment the concentration is at least 0.3 wt. %. In some embodiment the concentration is at least 0.5 wt. %. In some embodiment the concentration is at least 0.75 wt. %. In some embodiments, the concentration of the phosphonic acid, prior to addition to the mixture in which performic acid is formed, is not more than 70 wt. %. In some embodiments, the concentration is not more than 50 wt. %. In some embodiments, the concentration is not more than 35 wt. %. In some embodiments, the concentration is not more than 20 wt. %. In some embodiments, the concentration of the phosphonic acid, before addition to the mixture in which the performic acid is formed, is from 0.1%-70%. In some embodiments the concentration is from 0.2%-50%. In some embodiments the concentration is from 0.3-35%. In some embodiments the concentration is from 0.75%-25%. In some embodiments the concentration is from 0.5-20%. It will also be appreciated that in some cases, solid phosphonic acid, a salt thereof, or mixtures thereof, e.g. in granulated form, may be used. It will also be appreciated that the dissolution of solid phosphonic acid in water is endothermic, as is the dissolution of KOH, whereas the mixing of solutions of KOH and phosphonic or other dissolved acids is exothermic. Hence, persons skilled in the art will readily appreciate ways in which the order of addition of ingredients may be manipulated to achieved desired temperature effects.

Citric acid: in some embodiments, the concentration of citric acid, prior to addition to the mixture in which the performic acid is formed, is at least 0.1 wt. %. In some embodiments the concentration is at least 0.15 wt. %. In some embodiments the concentration is at least 0.2 wt. %. In some embodiments the concentration is at least 0.25 wt. %. In some embodiments the concentration is at least 0.3 wt. %. In some embodiments the concentration is at least 0.5 wt. %. In some embodiments the concentration is not more than 50 wt. %. In some embodiments the concentration is not more than 40 wt. %. In some embodiments the concentration is not more than 30 wt. %. In some embodiments the concentration is not more than 20 wt. %. In some embodiments the concentration is about 15 wt. %. In some embodiments the concentration of the citric acid, before addition to the mixture in which the performic acid is formed, is from 0.1%-50%. In some embodiments the concentration is from 0.15-40%. In some embodiments the concentration is from 0.2-30%. In some embodiments the concentration is from 0.25-20%. In some embodiments the concentration is from 0.3-10%. It will be appreciated that although in this example citric acid was used, other carboxylic acids may be used to the same effect, for example $C_2$-$C_7$ carboxylic acids such as propionic acid, lactic acid, salicylic acid, benzoic acid, glyceric acid, oxalic acid, tartaric acid, acetic acid, chloroacetic acid, dichloroacetic acid, trichloroacetic acid, and trifluoroacetic acid, and that these may be used in similar concentrations. Mixtures of carboxylic acids may also be used. It will also be appreciated, that as with phosphonic acid, the citric and/or other carboxylic acid may be provided in solid form and dissolved directly as needed.

Alkyl polyglycoside surfactant(s): alkyl polyglycoside surfactants for agricultural use are known in the art. In some embodiments, the total concentration of alkyl polyglycoside surfactants in the mixture in which the performic acid is formed, is at least 0.001 wt. %. In some embodiments the concentration is at least 0.01 wt. %. In some embodiments the concentration is at least 0.1 wt. %. In some embodiments the concentration is at least 1 wt. %. It will also be appreciated by persons skilled in the art that other surfactants may be substituted for or used in addition to the alkyl polyglycoside surfactant(s). Such surfactants may include amphoteric surfactants, cationic surfactants, non-ionic surfactants, and anionic surfactants.

The composition may be used as a disinfectant in and on food commodities, for soil, water, surfaces, equipment, air volumes, plant matter, and feed stocks, including disinfection and sterilization needs in all fields of application.

Example 21—More Compositions, e.g. for Arresting Sprouting in Potatoes

In a manner similar to that of Example 20, various compositions were formed. In some cases, as noted in the table below, one or more ingredients, such as formic acid, were left out of the composition and only added on-site prior to use. In some cases, phosphoric acid was used in addition to or instead of phosphonic acid. Such compositions were found to be stable and efficacious, for example in arresting sprouting of potatoes.

$H_2O_2$, phosphonic acid, citric acid, formic acid, surfactants: as in Example 19.

Phosphoric acid: in some embodiments, the total concentration of phosphoric acid, prior to addition to the mixture in which the performic acid is formed, is at least 0.1 wt. %. In some embodiments the concentration is at least 0.2 wt. %. In some embodiments the concentration is at least 0.3 wt. %. In some embodiments the concentration is at least 0.5 wt. %. In some embodiments the concentration is not more than 70 wt. %. In some embodiments the concentration is not more than 50 wt. %. In some embodiments the concentration is not more than 35 wt. %. In some embodiments the concentration is not more than 20 wt. %. In some embodiments, the concentration of phosphoric acid, before addition to the mixture in which the performic acid is formed, is from 0.1-70 wt. %. In some embodiments the concentration is from 0.2-50 wt. %. In some embodiments the concentration is from 0.3-35 wt. %. In some embodiments the concentration is from 0.5-20 wt. %. In some embodiments the concentration is around 10 wt. %.

|  | Formulation option no. | | | | | | | | |
| --- | --- | --- | --- | --- | --- | --- | --- | --- | --- |
|  | 1 | 2 | 3 | 4 | 5 | 6 | 7 | 8 | 9 |
| $H_2O_2$ | X | X | X | X | X | ** | ** | ** | — |
| Phosphonic acid | X | — | X | X | X | X | X | X | X |
| Phosphoric acid | — | X | X | — | X | — | — | — | — |
| Citric acid | X | X | X | X | X | X | — | ** | — |
| Formic acid | X | X | X | ** | ** | X | X | X | X |
| Surfactant | X | X | X | X | X | X | X | X | X |

In this table, X=included in the formulation, —=not included, and ** denotes a case in which the other ingredients are first mixed together, and then the indicated ingredient(s) is (are) added to this mixture on-site, not more than a few hours before use and in some cases immediately before use, optionally with heating of the formulation up to 80° C. for up to a few minutes.

In cases where control of insects and microorganisms, at least in part, by means of a controlled atmosphere (i.e. having a higher than normal $CO_2$ concentration) is desired, for example in storage rooms or silos, potassium bicarbonate may be added as well in order to generate additional $CO_2$;

such a method is particularly effective if application of the formulation will be made in a closed storage space via fogging or in the gas phase. Similarly, is gaseous ozone is used as an oxidizer to form performic acid in the gas phase, excess ozone can be supplied, as ozone itself may also help control pathogens.

Although the use of KOH to control the pH has so far been found to be best, other potassium, ammonium and sodium agents as well as combinations of all of these may be used. For example, potassium metabisulfite or potassium permanganate may be used as a well; these are also known to function as preservatives.

Example 22—Compliance with British/European Standard BS EN 1276:1997

This is a quantitative suspension test to evaluate the bactericidal activity of chemical disinfectants and antiseptics used in food, industrial, domestic and institutional areas. A mixture (Mixture 1) containing 51.65 wt. % deionized water, 21.4 wt. % of 47% aqueous KOH solution, 11.8 wt. % of 85% formic acid solution, 14.1 wt. % of 70% phosphonic acid solution, 1.0 wt. % Dequest® 2010 (1-hydroxyethylidene-1,1-diphosphonic acid), and 0.05 wt. % alkyl glycoside was prepared. To four parts by weight of Mixture 1 were mixed one part of 50% $H_2O_2$ solution. For testing, this mixture was further diluted 100-fold in water.

As is known in the art, EN 1276 defines a bactericidal product that has the capability to produce at least a $10^5$ reduction in the number of viable cells of the tested organisms, under defined experimental conditions. In the present case, a test suspension of bacteria in a solution of 0.3% bovine albumin (to act as an interfering substance) was added to the diluted product. The mixture was maintained at 20° C.-23° C. for 1 min. (the smallest of the recommended contact times according to the standard, which recommends longer contact times 10 or even 15 minutes), then the bactericidal action of the product was neutralized by the membrane filtration method, and the number of surviving bacteria was determined. Bacteria used were *Escherichia coli* (ATCC 8739), *Staphylococcus aureus* (ATCC 6538), *Pseudomonas aeruginosa* (ATCC 9027), and *Enterococcus hirae* (ATCC 10541). Each bacterial strain was maintained and counted by the pour plate method in accordance with EN 1276:1997. Experimental conditions were as follows:

| | |
|---|---|
| Test Temperature | 20° C. ± 0.5° C. |
| Concentration of test product | 1:99 |
| Contact time | 1 minute |
| Interfering substance | 3.0 g/l bovine albumin - dirty conditions |
| Neutralizing Method | Membrane Filtration |
| Temperature of incubation | 30° C. ± 1° C. |

The Membrane Filtration method was used for assessing the bactericidal effect of the product, and the results are summarized in the table immediately below.

| Test Organisms | Initial test suspension cells/ml (N) | No. of Surviving bacteria in 0.3% bovine albumin (Na) | Reduction in viability (R) |
|---|---|---|---|
| *E. coli* ATCC 8739 | $4.5 \times 10^8$ | Vc 0, 0<br>Na <$1.5 \times 10^2$ | >$10^5$ |
| *Staphylococcus aureus* ATCC 6538 | $1.1 \times 10^8$ | Vc 0, 0<br>Na <$1.5 \times 10^2$ | >$10^5$ |
| *Pseudomonas aeruginosa* ATCC 9027 | $3.0 \times 10^8$ | Vc 0, 0<br>Na <$1.5 \times 10^2$ | >$10^5$ |
| *Enterococcus hirae* ATCC 10541 | $1.0 \times 10^8$ | Vc 0, 0<br>Na <$1.5 \times 10^2$ | >$10^5$ |

Validation and verification of the methodology: Validation tests are summarized in the table immediately below. Verification of the methodology for each test organism shows that: (a) the number of cfu/ml of the bacterial test suspension is between $1.5 \times 10^8$ and $5.0 \times 10^8$ cfu/ml (N in the table above); (b) the number of cfu/ml of the bacterial suspension is between $6.0 \times 10^2$ and $3.0 \times 10^3$ cfu/ml (Nv in the table below); (c) the number of cfu/ml of the neutralizer toxicity control (B in the table below) is equal to, or greater than 0.05 times the number of cfu/ml of the bacterial suspension (Nv in the table below); (d) The number of cfu/ml of the dilution—neutralization control (C in the table below) is equal to, or greater than 0.5 times the number of cfu/ml of the neutralizer toxicity control (B in the table below); (e) the number of cfu/ml of the experimental condition validation (A in the table below) is equal to, or greater than 0.05 times of the number of cfu/ml of the bacterial suspension (Nv in the table below).

| Test Organism | Bacterial suspension | Experimental Conditions Control | Filtration Control | Membrane Filtration Neutralization Control | Bacterial test suspension (5.4.1.4) |
|---|---|---|---|---|---|
| *E. coli* ATCC 8739 | Vc: 311, 252<br>Nv: $2.8 \times 10^3$ | Vc: 247, 273<br>A: $2.6 \times 10^2$ | Vc: 227, 261<br>B: $2.4 \times 10^2$ | Vc: 258, 284<br>C: $2.7 \times 10^2$ | $4.5 \times 10^8$ |
| *Staphylococcus aureus* ATCC 6538 | Vc: 163, 158<br>Nv: $1.6 \times 10^3$ | Vc: 123, 145<br>A: $1.3 \times 10^2$ | Vc: 130, 144<br>B: $1.4 \times 10^2$ | Vc: 197, 143<br>C: $1.7 \times 10^2$ | $1.1 \times 10^8$ |
| *Pseudomonas aeruginosa* ATCC 9027 | Vc: 277, 307<br>Nv: $2.9 \times 10^3$ | Vc: 242, 281<br>A: $2.6 \times 10^2$ | Vc: 266, 303<br>B: $2.8 \times 10^2$ | Vc: 255, 278<br>C: $2.6 \times 10^2$ | $3.0 \times 10^8$ |
| *Enterococcus hirae* ATCC 10541 | Vc: 163, 197<br>Nv: $1.8 \times 10^3$ | Vc: 117, 156<br>A: $1.4 \times 10^2$ | Vc: 133, 176<br>B: $1.5 \times 10^2$ | Vc: 90, 122<br>C: $1.1 \times 10^2$ | $1.0 \times 10^8$ |

Vc = Viable Count;
Nv = Number of CFU/ml of the bacterial suspension;
A = Number of CFU/ml of the experimental conditions validation;
B = Number of CFU/ml of Neutralizer Toxicity Control;
C = Number of CFU/ml of the Dilution - Neutralization Control According to EN 1276, the tested composition possesses bactericidal activity in one minute at 20° C. under dirty conditions (3.0 g/l bovine albumin) for the tested reference strains.

Example 23—Compliance with British/European Standard BS EN 1650:1998

This is a quantitative suspension test to evaluate the activity of chemical disinfectants and antiseptics used in food, industrial, domestic and institutional areas against fungi, yeasts and molds. The same composition tested in Example 22 was tested in this case as well.

tures, strains and interfering substances are specified in the protocol for the standard, according to which the selection of the contact time to be used is 15 min+/−10 s; the actual 1 minute time used in the present test is listed as the shortest of several optional additional contact times, which range up to 60 min±10 s.)

Experimental conditions: test temperature 20° C.±0.5° C.; concentration of test product 1:99, diluted in water; contact time 1 minute; interfering substance 3.0 g/l bovine albumin; neutralizing solution 30 g/l saponin, 30 g/l polysorbate 80, 1 g/l L-histidine, 1 g/l L-cysteine; incubation temperature 30° C.+1° C.

Results are shown in the table immediately below.

| | | Validation test | | | | |
|---|---|---|---|---|---|---|
| Test organism | Fungal suspension | Experimental condition | Neutralizer toxicity or filtration control | Dilution Neutralization control or filtration test control | Fungal test suspension | Test procedure at concentration % (v/v) |
| Candida albicans ATCC 10231 | Vc: 88, 92 Nv: 9.0 × $10^2$ | Vc: 85, 93 A: 9.0 × $10^2$ | Vc: 94, 100 B: 1.0 × $10^2$ | Vc: 80, 83 C: 8.0 × $10^2$ | $10^{-5}$: 180, 200 $10^{-6}$: 10, 9 N: 1.9 × $10^7$ | Vc 0, 0 Na <1.5 × $10^2$ R >$10^4$ |
| Aspergillius niger ATCC 16404 | Vc: 154, 162 Nv: 1.6 × $10^3$ | Vc: 142, 151 A: 1.5 × $10^2$ | Vc: 150, 165 B: 1.6 × $10^2$ | Vc: 140, 150 C: 1.5 × $10^2$ | $10^{-5}$: 280, 300 $10^{-6}$: 50, 60 N: 2.9 × $10^7$ | Vc 0, 0 Na <1.5 × $10^2$ R >$10^4$ |
| Penecillium wild type | Vc: 123, 262 Nv: 1.2 × $10^3$ | Vc: 101, 93 A: 1.0 × $10^2$ | Vc: 89, 112 B: 1.1 × $10^2$ | Vc: 107, 107 C: 1.0 × $10^2$ | $10^{-5}$: 177, 169 $10^{-6}$: 21, 22 N: 1.7 × $10^7$ | Vc 0, 0 Na <1.5 × $10^2$ R >$10^4$ |

Vc = viable count;
R = reduction in viability;
Nv = number of cfu/ml of the fungal suspension;
N = number of cfu/ml of the fungal test suspension;
Na = number of cfu/ml in the test mixture;
A = number of cfu/ml of the experimental condition validation;
B = number of cfu/ml of the neutralizer toxicity validation or of the filtration control;
C = number of cfu/ml of the dilution-neutralization test control or of the membrane filtration test control As is known in the art, EN 1650 specifies a test method and the minimum requirements for anti-fungal, anti-yeast and anti-mold activity of chemical disinfectant and antiseptic products that form a homogeneous, physically stable preparation in hard water and that are used in food, industrial, domestic and institutional areas, excluding areas and situations where disinfection is medically indicated and excluding products used on living tissues except those for hand hygiene in the above-considered areas. In accordance with this standard, fungicidal activity is the capability of a product to produce at least a $10^4$ reduction in number of the vegetative yeast cells and mold spores belonging to the reference strains Candida albicans (ATCC 10231), Aspergillus niger (ATCC 16404) and Penecillium w.t. (wild type) under conditions defined by this standard.

A test suspension of yeast cells and/or mold spores in a solution of interfering substance (bovine albumin, 3 g/l) was added to a prepared sample of the product under test diluted in hard water. The mixture was maintained at 20° C.±1° C. for 1 min±10 s (required test conditions). After this contact time, an aliquot was taken; the fungicidal action in this portion was immediately neutralized or suppressed by a validated method. The method of choice was dilution-neutralization. (If a suitable neutralizer could be found, membrane filtration was used.) The number of surviving fungi, yeast cells or mold spores in each sample was determined and the reduction in viable counts was calculated. (Additional and optional exposure times, tempera- Thus according to EN 1650 the tested formulation possesses satisfactory fungicidal activity in 1 minute at 20° C. under dirty conditions (3 g/l bovine albumin) for the tested reference strains. In comparison, a commercial solution of peracetic acid (PAA, considered to be a very effective disinfectant and sterilizer) at 300 ppm (which is actually 100 ppm higher than the maximum permitted under the standard), tested against A. niger and Penicillium under the same test conditions, did not meet the standard. In fact, the formulation in accordance with the present invention was 10-100 times more effective than PAA in killing A. niger and Penicillium.

Example 24—Stability of Performic Acid Composition

Aqueous solutions of 50% $H_2O_2$ and 42% citric acid were mixed in a 3:2 ratio, yielding a mixture with 30 wt. % $H_2O_2$ and 16.8 wt. % citric acid. This was then mixed in a 1:1 ratio with Mixture 1 from Example 22. The resulting mixture was tested for stability by measuring the concentrations of $H_2O_2$ and formic acid over time. The loss of $H_2O_2$ over three months of storage at room temperature was about 0.5%, i.e. the $H_2O_2$ concentration was nearly unchanged over this period.

Example 25—Soil Treatment

Solutions were prepared according to the table below and used in amounts of 10.7 ml to treat 100 g of soil of pH 8 by mixing therein until a paste was obtained; except for trial 1, the soil was pre-wetted with 10.7 ml of water. Samples of soil were then taken for titration at the intervals shown. In the first table, units are wt. % unless noted otherwise.

|  | H2O2 | H3PO4 | HEDP | Ag Stab | Citric acid | Benzoic acid | EtOH | Glycerol |
|---|---|---|---|---|---|---|---|---|
| Trial 1 | 7 | 1.0 | 0.05 | 0.06 | 1000 ppm | 1000 ppm | 1 | 0 |
| Trial 2 | 7 | 1.0 | 0.05 | 0.06 | 1000 ppm | 1000 ppm | 1 | 0 |
| Trial 3 | 7 | 1.0 | 0.5 | 0.06 | 1000 ppm | 1000 ppm | 1 | 0 |
| Trial 4 | 7 | 3.5 | 0.3 | 0.06 | 1000 ppm | 1000 ppm | 1 | 0 |
| Trial 5 | 7 | 2.0 | 1.0 | 0.06 | 1000 ppm | 1000 ppm | 1 | 0 |
| Trial 6 | 7 | 3.5 | 1.0 | 0.06 | 1000 ppm | 1000 ppm | 1 | 0 |
| Trial 7 | 7 | 3.5 | 1.5 | 0.06 | 1000 ppm | 1000 ppm | 1 | 0 |
| Trial 8 | 7 | 3.5 | 1.0 | 0.06 | 1000 ppm | 1000 ppm | 0 | 2 |
| Trial 9 | 7 | 3.5 | 1.0 | 0.06 | 1000 ppm | 1000 ppm | 0 | 3 |
| Trial 10 | 7 | 2.0 | 1.0 | 0.06 | 1000 ppm | 1000 ppm | 0 | 3 |

|  | Time—minutes | | | | |
|---|---|---|---|---|---|
|  | 0 | 5 | 10 | 20 | 30 |
| Peroxide titration-% | 0.73 | 0.20 | 0.08 | 0.01 | 0.004 |
|  | 0.66 | 0.15 | 0.11 | 0.06 | 0.010 |
|  | 0.66 | 0.16 | 0.04 | 0.01 | 0.002 |
|  | 0.66 | 0.20 | 0.10 | 0.09 | 0.060 |
|  | 0.66 | 0.21 | 0.18 | 0.17 | 0.110 |
|  | 0.66 | 0.30 | 0.22 | 0.17 | 0.130 |
|  | 0.66 | 0.23 | 0.21 | 0.17 | 0.150 |
|  | 0.66 | 0.32 | 0.24 | 0.18 | 0.120 |
|  | 0.66 | 0.30 | 0.26 | 0.18 | 0.140 |
|  | 0.66 | 0.21 | 0.13 | 0.04 | 0.017 |

Example 26—Tests on Different Edible Materials and Substrates in Different Conditions The series of tables that follow below summarize numerous experiments that were conducted in accordance with embodiments of the invention. The following paragraphs explain the significance of the small letters that appear in the table.

Composition Preparation:

compositions (solutions) containing performic acid were prepared as discussed in the preceding examples; in some cases the compositions included one or more of the following groups: Emulsifiers, chelating agents, lubricants, corrosion inhibitors, anti foaming agents, inorganic additives, organic additives, modifiers, promoters, synergists, activators, solvents, essential oils, other ingredients, pH regulators, bases, acids, wetting agents, surfactants, stabilizers, catalysts, oxidizers, and performic Acid sources.

1a=pre-preparation of the composition at the manufacturing site;
1b=preparation by mixing on site
Method of Application:

As long as the compositions are in a liquid phase they may be applied them by immersing the substance to be treated in the compositions, and/or spraying the substance with the compositions, and/or creating a fog made of micro droplets using ultrasonic air pressure/liquid fogger and/or electric ultrasonic resonance, with or without heating, with or without ozone gas and/or ozonated water. The gas phase is introduced with a hot fogger with or without ozone gas.

2a Dipping; 2b pressure wash; 2c Spray; 2d Fog; 2e Gas; 2f mixing (when disinfecting water)

Formula Concentrations as $H_2O_2$ and or Ozone and or Peracetic Acid (PAA) Content in the Undiluted Concentrated Form:

Oxidizing levels are measured rapidly on site with a certified field kit. As of today there is no certified field kit to measure the performic acid (PFA) levels, so the inventor developed a standard measuring constant that correlates to the oxidation rate: using a Reflectoquant Colorimeter (Merck), the concentration of $H_2O_2$ and/or PAA was measured; a correlation constant was calculated to enable computation of the PFA concentration. As a parallel control titration of the solutions as described by Swern at al. (Organic Peroxides 1 (1970) p. 501) was conducted in a laboratory.

3a 35%-70%; 3b 20%-35%; 3c 10%-20%; 3d 0.1%-10%
Aims of Treatment:

4a Cleaning, Sanitizing, Disinfection, Sterilization—treatments are designed to dissolve and remove dirt and to act against microorganisms, including, among others, fungi, algae, mold, yeast, gram negative and gram positive bacteria, bacteriophages, viruses, amoebas, spores, protozoa, etc.; 4b Sprout arresting in potatoes—As well as for onion, garlic, sweet potato, radish in storage as well as elimination of emerging weeds; 4c Pre-harvest—The pre-harvest treatments are applications that aim to control pathogen attack through the soil and at the field—usually bush, and or orchard-trees, and/or greenhouse during the growing period; 4d Post-harvest—Post harvest treatments address the application of the composition on the substance itself, such as but not limited to fruits, vegetables, milk, milk products, meat, meat products, egg, and egg products—includes fertile egg for chicks produce, and or fish and or fish produce etc. Regarding fertile eggs that go through the hatching process, the disinfection treatments yielded 3-7% more hatched chicks; 4e Herbicide; 4f Insecticide, Miticide/acaricide, Nematocide; 4g Rodenticide; 4h Elimination of cut-end blackening, inducing whitening—such as but not limited to cut corn, celery, lettuce, French fries and all fresh cut produce, including chilled ready to eat salads and other chilled meals; 4i Improve storability and prolong shelf life—this addresses in a more specific category produce that is kept under long storage periods (weeks and months) that suffers losses during the storage period and later on: as the physiological age progresses, the produce becomes more prone to any stress, with the outcome being a very short shelf life; 4j Improve yield—this addresses seeds yield, orchard yield, soil yield after treatments, chick yield from fertilized eggs, etc.

Performance 5a 2%-4% losses; 5b 0%-2% losses; 5c higher yield 0.1%-60%; 5d Cleaning, Sanitizing, Disinfection, Sterilization efficacy Temperature 6a warmed solution 25-90° C.; 6b ambient solution 20-25° C.; 6c cooled solution 0.1-20° C.

Contact Time/Application Time:

contact time is the time the composition is in contact with the treated matter; application time is the time required for the solution to be applied to the matter. For example, a fruit is sprayed for 5 seconds (application time) and the solution is washed after 40 seconds of contact with the sprayed composition (contact time).

7a seconds; 7b minutes; 7c hours; 7d days

Intervals:

How often the compositions are applied 8a once; 8b a few times; 8c once a day; 8d once a week; 8e every two weeks; 8f once a month Method/Place of Post-Harvest Treatments 9a at the entry to the long storage and or to the packing house; 9b during storage before sorting line treatment; 9c on sorting line treatment; 9d during storage after sorting line treatment; 9e right before packing

| Fruit/Vegetable | Solution preparation | Application method | Formula concentration | Aim of treatment | Temperature | Contact time | interval | method of treatment | performance |
|---|---|---|---|---|---|---|---|---|---|
| Apple | 1a, b | 2a-e | 3c | 4a, b, c, d, i, j | 5b, c, d | 6b, c | 7a, b, c | 8b | 9a-e |
| Avocado | 1a, b | 2a-e | 3b | 4a, b, c, d, i, j | 5b, c, d | 6b, c | 7a, b | 8b | 9a-e |
| Citrus-Mandarin | 1a, b | 2a-e | 3a-d | 4a, c, d, i, j | 5b, c, d | 6a, b, c | 7a, b | 8b | 9a-e |
| Citrus-Oranges | 1a, b | 2a-e | 3a-d | 4a, c, d, i, j | 5b, c, d | 6a, b, c | 7a, b | 8b | 9a-e |
| Citrus-Mineola | 1a, b | 2a-e | 3a-d | 4a, c, d, i, j | 5b, c, d | 6a, b, c | 7a, b | 8b | 9a-e |
| Citrus-Grapefruits | 1a, b | 2a-e | 3a-d | 4a, c, d, i, j | 5b, c, d | 6a, b, c | 7a, b | 8b | 9a-e |
| Citrus-lemon | 1a, b | 2a-e | 3a-d | 4a, c, d, i, j | 5b, c, d | 6a, b, c | 7a, b | 8b | 9a-e |
| Date | 1a, b | 2c, d, e | 3c, d | 4a, c, d, i, j | 5b, c, d | 6b | 7a, b | 8a | 9c |
| Kiwi | 1a, b | 2a, c, d, e | 3c, d | 4a, c, d, i, j | 5b, c, d | 6b | 7a, b | 8b | 9a, d, e |
| Lychee | 1a, b | 2a, c, d, e | 3c, d | 4a, c, d, i, j | 5b, c, d | 6b | 7a, b | 8b | 9a, d, e |
| Mango | 1a, b | 2a-e | 3b, c, d | 4a, c, d, i, j | 5b, c, d | 6a, b | 7a, b | 8b | 9a-e |
| Peach | 1a, b | 2a, c, d, e | 3c, d | 4a, c, d, i, j | 5b, c, d | 6a | 7a, b | 8b | 9a, b, d, e |
| Pear | 1a, b | 2a, c, d, e | 3c, d | 4a, c, d, i, j | 5b, c, d | 6b | 7a, b | 8b | 9a, d, e |
| Persimmon | 1a, b | 2a-e | 3a-d | 4a, c, d, i, j | 5b, c, d | 6b | 7a, b | 8b | 9a-e |
| Pomegranate | 1a, b | 2a-e | 3a-d | 4a, c, d, i, j | 5b, c, d | 6a, b | 7a, b | 8b | 9a-e |
| Pepper | 1a, b | 2a-e | 3c, d | 4a, c, d, i, j | 5b, c, d | 6a, b | 7a, b | 8a | 9a |
| Asparagus | 1a, b | 2a, c, d, e | 3c, d | 4a, b, c, d, h, i, j | 5b, c, d | 6b, c | 7a, b, c | 8b | 9a-e |
| Banana | 1a, b | 2a, c, d, e | 3c, d | 4a, c, d, h, i, j | 5b, c, d | 6b, c | 7a, b | 8b | 9a-e |
| Broccoli | 1a, b | 2a, c, d, e | 3c, d | 4a, c, d, h, i, j | 5b, c, d | 6b, c | 7a, b, c | 8b | 9a-e |
| Cabbage | 1a, b | 2a-e | 3c, d | 4a, c, d, h, i, | 5b, c, d | 6b, c | 7a, b, c | 8b | 9a-e |
| Carrot | 1a, b | 2a-e | 3c, d | 4a, b, c, d, h, i, j | 5b, c, d | 6b, c | 7a, b, c | 8a | 9a-e |
| Cauliflower | 1a, b | 2a, c, d, e | 3c, d | 4a, c, d, h, i | 5b, c, d | 6b, c | 7a, b, c | 8b | 9a-e |
| Celery | 1a, b | 2a-e | 3c, d | 4a, b, c, d, h, i, j | 5b, c, d | 6b, c | 7a, b, c | 8b | 9a-e |
| Corn | 1a, b | 2a-e | 3a-d | 4a, c, d, h, i | 5b, c, d | 6b, c | 7a, b, | 8a | 9a |
| Kohlrabi | 1a, b | 2a-e | 3c, d | 4a, b, c, d, h, i, j | 5b, c, d | 6b, c | 7a, b, | 8b | 9a |
| Cucumber | 1a, b | 2a-e | 3c, d | 4a, c, d, h, i | 5b, c, d | 6b, c | 7a, b, | 8a | 9a |
| Eggplant | 1a, b | 2a-e | 3c, d | 4a, c, d, h, i | 5b, c, d | 6a, b | 7a, b, | 8a | 9a |
| Garlic | 1a, b | 2d, e | 3c, d | 4a, c, d, h, i, j | 5b, c, d | 6b, c | 7a, b, | 8b | 9a |
| Lettuce | 1a, b | 2a-e | 3c, d | 4a, b, c, d, h, i, j | 5b, c, d | 6b, c | 7a, b, | 8a | 9a, b, c, e |
| Onion | 1a, b | 2d, e | 3a-d | 4a, c, d, h, i, j | 5b, c, d | 6b, c | 7a, b, c | 8b | 9a-e |
| Peanuts | 1a, b | 2a-e | 3a-d | 4a, c, d, h, j | 5b, c, d | 6b | 7a, b, c | 8a | 9a |
| Potato | 1a, b | 2a-e | 3a-d | 4a, b, c, d, h, i, j | 5b, c, d | 6b, c | 7a, b, c | 8b | 9a-e |
| Strawberry | 1a, b | 2a, c, d, e | 3c, d | 4a, c, d, h, i | 5b, c, d | 6b, c | 7a, b, | 8b | 9a |
| Sweet pepper | 1a, b | 2a-e | 3c, d | 4a, c, d, h, i | 5b, c, d | 6a, b, | 7a, b, | 8a | 9a |
| Sweet potato | 1a, b | 2a-e | 3d | 4a, b, c, d, h, i, j | 5b, c, d | 6a, b, c | 7a, b, c | 8b | 9a-e |
| Tomato | 1a, b | 2a-e | 3d | 4a, c, d, h, i | 5b, c, d | 6b | 7a, b, | 8b | 9a-e |
| Water melon | 1a, b | 2a-e | 3c, d | 4a, c, d, h, i | 5b, c, d | 6b | 7a, b, | 8a | 9a |
| Grapes | 1a, b | 2a-e | 3c, d | 4a, c, d, h, i | 5b, c, d | 6b | 7a, b, | 8a | 9a |

| Field Pathogen | Solution preparation | Application method | Formula concentration | Aim of treatment | temperature | Contact time | interval | method of treatment | performance |
|---|---|---|---|---|---|---|---|---|---|
| Phytophthora | 1a, b | 2a-e | 3a-d | 4a, c, d, f, h, i, j | 5b, c, d | 6a, b, c | 7a, b, | 8b | 9a-e |
| Scab | 1a, b | 2a-e | 3a-d | 4a, c, d, f, h, i, j | 5b, c, d | 6a, b, c | 7a, b, | 8b | 9a-e |
| Silver Scurf | 1a, b | 2a-e | 3a-d | 4a, c, d, f, h, i, j, | 5b, c, d | 6a, b, c | 7a, b, | 8b | 9a-e |
| Penecillium | | | | | | | | | |
| Butrytice | | | | | | | | | |
| *Alternaria* | | | | | | | | | |
| *Aspergillus* | | | | | | | | | |
| Candida | | | | | | | | | |
| Rizopus | | | | | | | | | |

-continued

| Seed or grain | Solution preparation | Application method | Formula concentration | Aim of treatment | temperature | Contact time | interval | method of treatment | performance |
|---|---|---|---|---|---|---|---|---|---|
| Flower bulbs | 1a, b | 2a, c, d, e | 3c, d | 4a, c, d, i, j | 5b, c, d | 6a, b, c | 7a, b, c | 8a, b | 9a-e |
| Barley | 1a, b | 2a-e | 3a-d | 4a, c, d, i, j | 5b, c, d | 6a, b, c | 7a, b, c | 8a, b | 9a, d, e |
| Oats | 1a, b | 2a-e | 3a-d | 4a, c, d, i, j | 5b, c, d | 6a, b, c | 7a, b, c | 8a, b | 9a, d, e |
| Potato | 1a, b | 2a, c, d, e | 3a-d | 4a, b, c, d, f, h, i, j | 5b, c, d | 6a, b, c | 7a, b, c | 8a, b | 9a, d, e |
| Wheat | 1a, b | 2a-e | 3a-d | 4a, c, d, i, j | 5b, c, d | 6a, b, c | 7a, b, c | 8a, b | 9a, d, e |
| Soybeans | 1a, b | 2a-e | 3a-d | 4a, c, d, i, j | 5b, c, d | 6a, b, c | 7a, b, c | 8a, b | 9a, d, e |
| Corn | 1a, b | 2a-e | 3a-d | 4a, c, d, i, j | 5b, c, d | 6a, b, c | 7a, b, c | 8a, b | 9a, d, e |
| Tomato | 1a, b | 2a, c, d, e | 3a-d | 4a, c, d, i, j | 5b, c, d | 6a, b, c | 7a, b, c | 8a, b | 9a, d, e |
| Onion | 1a, b | 2a, c, d, e | 3a-d | 4a, c, d, i, j | 5b, c, d | 6a, b, c | 7a, b, c | 8a, b | 9a, d, e |
| Garlic | 1a, b | 2a, c, d, e | 3a-d | 4a, c, d, i, j | 5b, c, d | 6a, b, c | 7a, b, c | 8a, b | 9a, d, e |
| Rice | 1a, b | 2a-e | 3a-d | 4a, c, d, i, j | 5b, c, d | 6a, b, c | 7a, b, c | 8a, b | 9a, d, e |
| Pepper | 1a, b | 2a, c, d, e | 3a-d | 4a, c, d, i, j | 5b, c, d | 6a, b, c | 7a, b, c | 8a, b | 9a, d, e |
| Melons | 1a, b | 2a-e | 3a-d | 4a, c, d, i, j | 5b, c, d | 6a, b, c | 7a, b, c | 8a, b | 9a, d, e |
| Cucumber | 1a, b | 2a, c, d, e | 3a-d | 4a, c, d, i, j | 5b, c, d | 6a, b, c | 7a, b, c | 8a, b | 9a, d, e |
| Cotton | 1a, b | 2a-e | 3a-d | 4a, c, d, i, j | 5b, c, d | 6a, b, c | 7a, b, c | 8a, b | 9a, d, e |
| Vegetative propagation | 1a, b | 2a, c, d, e | 3c, d | 4a, c, d, i, h, j | 5b, c, d | 6b, c | 7a, b, | 8a, b | 9a, d, e |
| Flower seedling | 1a, b | 2a, c, d, e | 3c, d | 4a, c, d, i, h, j | 5b, c, d | 6b, c | 7a, b, | 8a, b | 9a, d, e |
| Ornamental plant seedling | 1a, b | 2a, c, d, e | 3c, d | 4a, c, d, i, h, j | 5b, c, d | 6b, c | 7a, b, | 8a, b | 9a, d, e |

| | Solution preparation | Application method | Formula concentration | Aim of treatment | temperature | Contact time | interval | method of treatment | performance |
|---|---|---|---|---|---|---|---|---|---|
| For soil disinfection | 1a, b | 2a-e | 3a-d | 4a, b, c, d, e, f, g, i, j | 5b, c, d | 6a, b, c | 7a, b, c, d | 8a, b | N/A |
| For disinfection of substrate for sowing | 1a, b | 2a-e | 3a-d | 4a, b, c, d, e, f, g, i, j | 5b, c, d | 6a, b, c | 7a, b, c, d | 8a, b | N/A |
| As herbicide | 1a, b | 2a-e | 3a-d | 4a, b, c, d, i, j | 5b, c, d | 6a, b, c | 7a, b, c, d | 8a, b, | N/A |
| As insecticide | 1a, b | 2a-e | 3a-d | 4a, c, d, i, j | 5b, c, d | 6a, b, c | 7a, b, c, d | 8a, b, | 9a, d, e |
| As rodenticide | 1a, b | 2a-e | 3a-d | 4a, c, d, i, j | 5b, c, d | 6a, b, c | 7a, b, c, d | 8a, b | 9a, d, e |

| Micro-organism | Solution preparation | Application method | Formula concentration | Aim of treatment | temperature | Contact time | interval | method of treatment | performance |
|---|---|---|---|---|---|---|---|---|---|
| Gram positive bacteria | 1a, b | 2a-e | 3a-d | 4a, c, d, h, i, j | 5b, c, d | 6a, b, c | 7a, b, | 8a, b | 9a-e |
| Gram negative bacteria | 1a, b | 2a-e | 3a-d | 4a, c, d, h, i, j | 5b, c, d | 6a, b, c | 7a, b, | 8a, b | 9a-e |
| Fungi | 1a, b | 2a-e | 3a-d | 4a, c, d, h, i, j | 5b, c, d | 6a, b, c | 7a, b, | 8a, b | 9a-e |
| Algae | 1a, b | 2a-e | 3a-d | 4a, c, d, h, i, j | 5b, c, d | 6a, b, c | 7a, b, | 8a, b | 9a-e |
| Virus | 1a, b | 2a-e | 3a-d | 4a, c, d, h, i, j | 5b, c, d | 6a, b, c | 7a, b, | 8a, b | 9a-e |
| Yeast | 1a, b | 2a-e | 3a-d | 4a, c, d, h, i, j | 5b, c, d | 6a, b, c | 7a, b, | 8a, b | 9a-e |
| Mold | 1a, b | 2a-e | 3a-d | 4a, c, d, h, i, j | 5b, c, d | 6a, b, c | 7a, b, | 8a, b | 9a-e |
| Spores | 1a, b | 2a-e | 3a-d | 4a, c, d, h, i, j | 5b, c, d | 6a, b, c | 7a, b, | 8a, b | 9a-e |
| Bacteriophage | 1a, b | 2a-e | 3a-d | 4a, c, d, h, i, j | 5b, c, d | 6a, b, c | 7a, b, | 8a, b | 9a-e |
| protozoa | 1a, b | 2a-e | 3a-d | 4a, c, d, h, i, j | 5b, c, d | 6a, b, c | 7a, b, | 8a, b | 9a-e |

| Type of water | Solution preparation | Application method | Formula concentration | Aim of treatment | temperature | Contact time | interval | method of treatment | performance |
|---|---|---|---|---|---|---|---|---|---|
| General | 1a, b | 2e, f | 3a-d | 4a, b, c, i, j | 5d | 6a, b, c | 7a, b, c | 8a, b | 9a-e |
| Recirculated | 1a, b | 2e, f | 3a-d | 4a, b, c, i, j | 5d | 6a, b, c | 7a, b, c | 8a, b | 9a-e |
| Drinking water | 1a, b | 2e, f | 3a-d | 4a, b, c, i, j | 5d | 6a, b, c | 7a, b, c | 8a, b | 9a-e |

| Foliage | Solution preparation | Application method | Formula concentration | Aim of treatment | temperature | Contact time | interval | method of treatment | performance |
|---|---|---|---|---|---|---|---|---|---|
| Foliage freshness | 1a, b | 2a-e | 3a-d | 4a, c, d, f, i, j | 5b, c, d | 6a, b, c | 7a, b, c | 8a | 9a-e |
| Stem cleaning | 1a, b | 2a-e | 3a-d | 4a, c, d, f, h, i, j, | 5b, c, d | 6a, b, c | 7a, b, | 8a | 9a-e |

| | | | | | | | | | |
|---|---|---|---|---|---|---|---|---|---|
| Stem freshness | 1a, b | 2a-e | 3a-d | 4a, c, d, f, h, i, j, | 5b, c, d | 6a, b, c | 7a, b, | 8a | 9a-e |
| Field foliage | 1a, b | 2a-e | 3a-d | 4a, c, d, f, i, j, | 5b, c, d | 6a, b, c | 7a, b, c, d | 8a, b | N/A |

| General foods | Solution preparation | Application method | Formula concentration | Aim of treatment | temperature | Contact time | interval | method of treatment | performance |
|---|---|---|---|---|---|---|---|---|---|
| Fish | 1a, b | 2a-e | 3a-d | 4a, c, d, i, j | 5b, c, d | 6a, b, c | 7a, b, c | 8a, b | 9a-e |
| Eggs (to eat) | 1a, b | 2a, c, d, e | 3a-d | 4a, c, d, i, h, j | 5b, c, d | 6a, b, c | 7a, b, c | 8a, b | 9a-e |
| Meat | 1a, b | 2a-e | 3a-d | 4a, c, d, i, j | 5b, c, d | 6a, b, c | 7a, b, c | 8a, b | 9a-e |
| Milk | 1a, b | 2a-e | 3a-d | 4a, c, d, i, j | 5b, c, d | 6a, b, c | 7a, b, c | 8a, b | 9a-e |
| Milk products | 1a, b | 2a-e | 3a-d | 4a, c, d, i, j | 5b, c, d | 6a, b, c | 7a, b, c | 8a, b | 9a-e |
| Eggs (to hatch) | 1a, b | 2a, c, d, e | 3a-d | 4a, c, d, i, j | 5b, c, d | 6a, b, c | 7a, b, c, d | 8a, b, c | 9a-e |

| Disinfecting surfaces, spaces, equipment & systems | Solution preparation | Application method | Formula concentration | Aim of treatment | temperature | Contact time | interval | method of treatment | performance |
|---|---|---|---|---|---|---|---|---|---|
| Food industry | 1a, b | 2a-e | 3a-d | 4a, f, g, | 5d | 6a, b, c | 7a, b, c | 8a, b, c | 9a-e |
| Hospitals | 1a, b | 2a-e | 3a-d | 4a, f, g, | 5d | 6a, b, c | 7a, b, c | 8a, b, c | N/A |
| Hotels | 1a, b | 2a-e | 3a-d | 4a, f, g, | 5d | 6a, b, c | 7a, b, c | 8a, b, c | N/A |
| Public places | 1a, b | 2a-e | 3a-d | 4a, f, g, | 5d | 6a, b, c | 7a, b, c | 8a, b, c | N/A |
| Production halls | 1a, b | 2a-e | 3a-d | 4a, f, g, | 5d | 6a, b, c | 7a, b, c | 8a, b, c | 9a-e |
| Buses | 1a, b | 2a-e | 3a-d | 4a, f, g, | 5d | 6a, b, c | 7a, b, c | 8a, b, c | N/A |
| Airplanes | 1a, b | 2a-e | 3a-d | 4a, f, g, | 5d | 6a, b, c | 7a, b, c | 8a, b, c | N/A |
| Trains | 1a, b | 2a-e | 3a-d | 4a, f, g, | 5d | 6a, b, c | 7a, b, c | 8a, b, c | N/A |
| Spaces | 1a, b | 2a-e | 3a-d | 4a, f, g, i, j | 5b, c, d | 6a, b, c | 7a, b, c | 8a, b, c | 9a-e |

Example 27—Compliance with British/European Standard BS EN 1276:2009

This is a quantitative suspension test to evaluate the bactericidal activity of chemical disinfectants and antiseptics used in food, industrial, domestic and institutional areas. A first and a second mixture were mixed together in a ratio of 40 wt. % first mixture and 60 wt. % second mixture, along with phosphonic acid. The first mixture contained 80 wt. % of a 94 wt. % aqueous formic acid solution and 20 wt. % of a 99 wt. % propionic acid solution. The second mixture was a 50 wt. % hydrogen peroxide solution. For testing, this mixture was further diluted 1000-fold in water; the resulting dilute solution (which contained about 800 ppm of phosphonic acid) had a pH of approximately 2.5.

As is known in the art, EN 1276 defines a bactericidal product that has the capability to produce at least a $10^5$ reduction in the number of viable cells of the tested organisms, under defined experimental conditions. In the present case, a test suspension of bacteria (*Lysteria monocytogenes*, ATCC 19115) in a solution of 3 g/l bovine albumin (to act as an interfering substance) was added to the diluted product. The mixture was maintained at 20° C.±0.5° C. for 1 min. or 5 min., then the bactericidal action of the product was neutralized by addition/dilution (solution containing 6 g/l sodium thiosulfate, 30 g/l polysorbate 80 and 3 g/l lecithin), and the number of surviving bacteria was determined. Each bacterial strain was maintained and counted by the pour plate method in accordance with EN 1276:1997. The results were as follows (Vc=viable count, N=number of cfu/ml of the bacterial suspension, Na=number of cfu in the test mixture, R=reduction in viability):

| Contact time | Initial test suspension cells/ml (N) | No. of Surviving bacteria in 0.3% bovine albumin (Na) | Reduction in viability (R) |
|---|---|---|---|
| 1 minute | $2.2 \times 10^8$ | Vc 0, 0<br>Na <$1.4 \times 10^2$ | >$10^5$ |
| 5 minutes | $2.2 \times 10^8$ | Vc 0, 0<br>Na <$1.4 \times 10^2$ | >$10^5$ |

Validation and verification of the methodology: the validation tests are summarized in the table immediately below.

| Contact time | Bacterial suspension | Experimental Conditions Control | Neutralization toxicity Control | Dilution Neutralization Control | Bacterial test suspension |
|---|---|---|---|---|---|
| 1 minute | Vc: 158, 149<br>Nv: $1.5 \times 10^3$ | Vc: 67, 79<br>A: $7.3 \times 10^2$ | Vc: 49, 68<br>B: $6.8 \times 10^1$ | Vc: 46, 68<br>C: $4.6 \times 10^1$ | $10^{-6}$: 234, 232<br>$10^{-7}$: 20, 24 |
| 5 minutes | Vc: 120, 122<br>Nv: $1.2 \times 10^3$ | Vc: 54, 76<br>A: $6.5 \times 10^2$ | Vc: 35, 50<br>B: $4.3 \times 10^1$ | Vc: 54, 62<br>C: $5.8 \times 10^1$ | N: $2.2 \times 10^8$ |

Vc = Viable Count;
Nv = Number of CFU/ml of the bacterial suspension;
A = Number of CFU/ml of the experimental conditions validation;
B = Number of CFU/ml of Neutralization Toxicity Control;
C = Number of CFU/ml of the Dilution-Neutralization Control These results show that this composition conforms to the requirements of EN 1276 for the evaluation of bactericidal activity in 1 minute and 5 minutes at 20° C., under dirty conditions (3 g/l bovine albumin) for reference strain *Listeria monocytogenes*.

Example 28—Compliance with British/European Standard BS EN 13697:2001

This is a quantitative non-porous surface test to evaluate the bactericidal and/or fungicidal activity of chemical disinfectants used in food, industrial, domestic and institutional areas. The composition used was the same composition described in Example 22; as in Example 22, for testing it was diluted 100-fold.

As is known in the art, EN 13697 specifies a test method for testing the efficacy of materials against microorganisms on surfaces. A test suspension of fungi in solution under dirty conditions is inoculated onto a stainless steel surface and dried. The prepared sample of the product is applied in a manner which covers the dried film. The surface is maintained at a specified temperature for the defined contact time. The surface is transferred to the neutralization medium. The number of surviving organisms which can be recovered from the surface is determined. Dilution-neutralization is also utilized in parallel in some of the samples.

The fungal strain was maintained and counted by the pour plate method in accordance with EN 13697:2001. Experimental conditions: test temperature, 22° C.±1° C.; contact times 1 minute and 5 minutes; hard water (distilled, not demineralized water), per total volume of 1000 ml: 0.12 g of anhydrous $MgCl_2$, 0.28 g of anhydrous $CaCl_2$, and 0.28 g of $NaHCO_3$ were added; interfering substance: 3.0 g/l bovine albumin—dirty conditions; neutralizer: 6 g/l sodium thiosulphate+30 g/lpolysorbate 80+lecithin 3 g/l; temperature of incubation 30° C.±1° C.; test surface: stainless steel discs (2 cm diameter); test procedure: dilution-neutralization method was used to assess the fungicidal effect of the product, and the results are summarized in the table below.

| Fungal test suspension | Validation test | | Water control | Test results | |
|---|---|---|---|---|---|
| N | NT | NC | Nc | 1 min | 5 min |
| $10^{-5}$; >300, >300 | $10^{-2}$: >300, >300 | $10^{-2}$: >300, >300 | $10^{-2}$: 25, 27 | $10^{-0}$: 0, 0 | $10^{-0}$: 0, 0 |
| $10^{-6}$: 40, 46 | $10^{-3}$: 35, 37 | $10^{-3}$: 68, 63 | $10^{-3}$: 2, 3 | $10^{-1}$: 0, 0 | $10^{-1}$: 0, 0 |
| N: 6.33 | $10^{-4}$: 2, 5 | $10^{-4}$: 8, 5 | $10^{-4}$: 0, 0 | $10^{-2}$: 0, 0 | $10^{-2}$: 0, 0 |
| | NT: 5.56 | NT: 5.82 | $10^{-5}$: 0, 0 | Nd <0.1 | Nd <0.1 |
| | | | Nc: 4.41 | Nts:0 | Nts:0 |
| | | | Nts: 22 | ME: >4.40 | ME: >4.40 |

N = $Log_{10}$ number of cfu per 0.05 ml of the test suspension; NT = $Log_{10}$ number of cfu per test surface of the neutralization test; NC = $Log_{10}$ number of cfu per test surface of the neutralization control; Nc = $Log_{10}$ number of cfu per test surface in the water control; Nd = $Log_{10}$ number of cfu per test surface in the disinfectant test; Nts = number of cfu remaining on the test surface; ME = microbicidal effect.

Thus in accordance with EN 13697, the product, KEF 1, possesses fungicidal activity on surfaces in 1 min and in 5 min at 22° C. under dirty conditions (3 g/l bovine albumin) for reference strain of *Aspergillus brasiliensis*.

It is to be understood that both the foregoing general description and the following detailed description are exemplary and explanatory only and are not restrictive of the invention, as claimed. Although the foregoing invention has been described in some detail for purposes of illustration, it will be readily apparent to one skilled in the art that changes and modifications may be made without departing from the scope of the invention described herein.

What is claimed is:

1. A method for protecting edible matter from decay, comprising contacting edible matter or a substrate therefor with a composition comprising:
   (1) water,
   (2) at least one of: (a) phosphonic acid ($HP(O)(OH)_2$) or a salt thereof and (b) phosphoric acid,
   (3) a carboxylic acid,
   (4) a surfactant,
   (5) at least one of: (i) a performic acid source and (ii) an oxidizer which can oxidize said performic acid source to performic acid, and
   (6) performic acid
said contacting being
   (i) for a time and
   (ii) in an amount of composition and/or at a concentration of composition sufficient to protect said edible matter from said decay, wherein the composition is such that at a concentration of 20 ppm performic acid and a contact time of up to one minute at room temperature, the composition achieves a 10000-fold (4 log) reduction in the cfu of a pathogen grown on a designed growth medium, wherein the pathogen is at least one of the pathogens in the group consisting of *Escherichia coli* (ATCC 8739), *Staphylococcus aureus* (ATCC 6538), *Pseudomonas aeruginosa* (ATCC 9027), *Enterococcus hirae* (ATCC 10541), *Candida albicans* (ATCC 10231), *Aspergillus niger* (ATCC 16404), *Listeria monocytogenes* (ATCC 19115) and *Penecillium* w.t. (wild type).

2. The method of claim 1, wherein said method comprises contacting edible matter with said composition.

3. The method of claim 1, wherein said method comprises contacting a substrate for said edible matter with said composition.

4. The method of claim 3 wherein with a one-minute contact time the composition meets or exceeds at least one of the following Standards: BS EN 1276:1997, BS EN 1650:1998, BS EN 13697:2001, BS EN 1276:2009.

5. The method of claim 4, wherein the composition achieves a 100000-fold (5 log) reduction in the cfu of a pathogen grown on a designed growth medium within one minute at 20° C. under dirty conditions of 3.0 g/l bovine albumin, wherein the pathogen is one or more of the reference strains *Listeria monocytogenes* (ATCC 19115), (ATCC 8739), *Staphylococcus aureus* (ATCC 6538), *Pseudonionas aeruginosa* (ATCC 9027) and *Enterococcus hirae* (ATCC 10541).

6. The method of claim 4, wherein the composition exceeds at least one of (a) Standard BS EN 1650:1998 and (b) BS EN 13697:2001.

7. The method of claim 6, wherein the composition possesses fungicidal activity within one minute at 20° C. under dirty conditions of 3.0 g/l bovine albumin for one or more of the reference strains *Candida albicans, Aspergillus brasiliensis (Aspegillus niger)*, and *Penicillium* w.t.

8. The method of claim 3 wherein the carboxylic acid contains from 2 to 7 carbon atoms.

9. The method of claim 8 wherein the carboxylic acid is selected from the group consisting of citric acid, propionic acid, lactic acid, salicylic acid, benzoic acid, glyceiic acid, oxalic acid, tartaric acid, acetic acid, chloroacetic acid, dichloroacetic acid, trichloroacetic acid, and trifluoroacetic acid.

10. The method of claim 9 wherein the carboxylic acid is selected from the group consisting of citric acid, lactic acid, propionic acid and mixtures thereof.

11. The method according to claim 3 wherein the concentration of performic acid in said composition decreases by not more than 1% over 6 months at a temperature at or below 20° C.

12. The method of claim 3, wherein, if hydrogen peroxide is present in the composition, the ratio of performic acid to hydrogen peroxide is less than 4:1.

13. The method of claim 3, wherein the composition does not contain both alkyl ester peroxycarboxylic acid and a $C_2$ or higher alcohol.

14. The method of claim 4 wherein the composition exceeds at least one of Standard BS EN 1276:1997 and BS EN 1276:2009.

15. The method of claim 5 wherein the composition processes bactericidal activity within one minute at 20° C. under dirty conditions of 3.0 g/l bovine albumin for the reference strains *E. coli* (ATCC 8739), *Staphylococcus aureus* (ATCC 6538), *Pseudomonas aeruginosa* (ATCC 9027) and *Enterococcus hirae* (ATCC 10541).

16. The method of claim 4 wherein the composition has bactericidal activity against gram-positive bacteria.

17. The method of claim 4 wherein the composition has bactericidal activity against gram-negative bacteria.

18. The method of claim 3 wherein the concentration of said performic acid is from 1 ppb to 1000 ppm.

19. The method of claim 2 wherein with a one-minute contact time the composition meets or exceeds at least one of the following Standards: BS EN 1276:1997, BS EN 1650:1998, BS EN 13697:2001, BS EN 1276:2009.

20. The method of claim 19, wherein the composition achieves a 100000-fold (5 log) reduction in the cfu of a pathogen grown on a designed growth medium within one minute at 20° C. under dirty conditions of 3.0 g/l bovine albumin, wherein the pathogen is one or more of the reference strains *Listeria monocytogenes* (ATCC 19115), *E. coli* (ATCC 8739), *Staphylococcus aureus* (ATCC 6538), *Pseudomonas aeruginosa* (ATCC 9027) and *Enterococcus hirae* (ATCC 10541).

21. The method of claim 19 wherein the composition exceeds at least one of (a) Standard BS EN 1650:1998 and (b) BS EN 13697:2001.

22. The method of claim 21, wherein the composition possesses fungicidal activity within one minute at 20° C. under dirty conditions of 3.0 g/l bovine albumin for one or more of the reference strains *Candida albicans, Aspergillus brasiliensis (Aspergillus niger)*, and *Penecilium* w.t.

23. The method of claim 2 wherein the carboxylic acid contains from 2 to 7 carbon atoms.

24. The method of claim 23 wherein the carboxylic acid is selected from the group consisting of citric acid, propionic acid, lactic acid, salicylic acid, benzoic acid, glyceric acid, oxalic acid, tartaric acid, acetic acid, chloroacetic acid, dichloroacetic acid, trichloroacetic acid, and trifluoroacetic acid.

25. The method of claim 24 wherein the carboxylic acid is selected from the group consisting of citric acid, lactic acid, propionic acid and mixtures thereof.

26. The method of claim 2 wherein said composition contains phosphonic acid, a salt thereof, or a mixture of phosphonic acid and a salt thereof in a concentration of 0.5 to 98 wt. %.

27. The method according to claim 2 wherein said surfactant is an alkyl polyglycoside.

28. The method according to claim 2 wherein said performic acid source is selected from the group consisting of formic acid, formic acid esters, and formic acid salts.

29. The method according to claim 2 wherein said phosphoric acid is present in a concentration of 0.00001 to 98 wt. %.

30. The method of claim 2 wherein said oxidizer is selected from the group consisting of inorganic peroxides, nitrates, halogens and halogen compounds, hypohalite compounds, ozone, oxides, permanganate salts, multivalent chromium compounds, acids, sulfides and Tollens' reagent.

31. The method according to claim 2 wherein the oxidizer is selected from the group consisting of hydrogen peroxide, sodium percarbonate, sodium periodate, sodium persulfate, ammonium persulfate, sodium perborate, sodium peroxide, calcium peroxide, silver (II) oxide, chlorine dioxide, diacyl peroxides, ketone peroxides, peroxydicarbonates, peroxyesters, dialkyl peroxides, hydroperoxides, peroxyketals, urea hydrogen peroxide, ammonium hydrogen peroxide, ozone, sodium peroxydisulfate, potassium peroxydisulfate and ammonium peroxydisulfate.

32. The method according to claim 2 wherein the concentration of performic acid in said composition decreases by not more than 1% over 6 months at a temperature at or below 20° C.

33. The method according to claim 32 wherein the concentration of performic acid in said composition decreases by not more than 1% over 6 months at a temperature of 20° C.

34. The method of claim 2, wherein, if hydrogen peroxide is present in the composition, the ratio of performic acid to hydrogen peroxide is less than 4:1.

35. A method for protecting a fruit or vegetable from the growth of one or more members of the group consisting of *Escherichia coli, Staphylococcus aureus, Pseudomonas aeruginosa, Enterococcus hirae, Candida albicans, Aspergillus niger, Listeria monocytogenes* and *Penecillium*, comprising contacting said fruit or vegetable with a composition comprising:
  (1) water,
  (2) at least one of: (a) phosphonic acid ($HP(O)(OH)_2$) or a salt thereof and (b) phosphoric acid,
  (3) a carboxylic acid,
  (4) a surfactant,
  (5) at least one of: (i) a performic acid source and (ii) an oxidizer which can oxidize said performic acid source to performic acid, and
  (6) performic acid,
said contacting being
  (i) for a time and
  (ii) in an amount of composition and/or at a concentration of composition sufficient to protect said edible matter from said growth, wherein the composition is such that at a concentration of 20 ppm performic acid and within one minute contact time at room temperature, the composition achieves the following (a), (b), or (a) and (b): (a) a 10000-fold (4 log) reduction in the cfu of a pathogen grown on a designed growth medium, wherein the pathogen is at least one of the pathogens in the group consisting of *Candida albicans* (ATCC 10231), *Aspergillus niger* (ATCC 16404), and *Penecillium* w.t. (wild type), (b) a 100000-fold (5 log) reduction in the cfu of a pathogen grown on a designed growth medium, wherein the pathogen is at least one of the pathogens in the group consisting of *Escherichia coli* (ATCC 8739), *Staphylococcus aureus* (ATCC 6538), *Pseudomonas aeruginosa* (ATCC 9027), *Enterococcus hirae* (ATCC 10541), and *Listeria monocytogenes*.

36. The method of claim 35, wherein the composition does not contain both alkyl ester peroxycarboxylic acid and a $C_2$ or higher alcohol.

37. The method of claim 2, wherein the composition does not contain both alkyl ester peroxycarboxylic acid and a $C_2$ or higher alcohol.

38. The method of claim 19 wherein the composition exceeds at least one of Standard BS EN 1276:1997 and BS EN 1276:2009.

39. The method of claim 20 wherein the composition possesses bactericidal activity within one minute at 20° C. under dirty conditions of 3.0 g/l bovine albumin for the reference strains *E. coli* (ATCC 8739), *Staphylococcus aureus* (ATCC 6538). *Pseudomonas aeruginosa* (ATCC 9027) and *Enterococcus hirae* (ATCC 10541).

40. The method of claim 19 wherein the composition has bactericidal activity against gram-positive bacteria.

41. The method of claim 19 wherein the composition has bactericidal activity against gram-negative bacteria.

42. The method of claim 2 wherein said edible matter is selected from the group consisting of fruits, vegetables, grains, sprouts, nuts, seeds, meats, meat products, milk, milk products, fish, poultry, eggs, and mixtures thereof.

43. The method of claim 42 wherein said edible matter is selected from the group consisting of fruits and vegetables.

44. The method of claim 2, wherein the mass of performic acid (PFA) which is contacted with said edible matter is not more than 0.0001 times the mass of the edible matter.

45. The method of claim 2, wherein the ratio of the mass of the PFA which is contacted with said edible matter to the volume of said edible matter is not more than 1 g per 0.1 m³.

46. The method of claim 2 wherein the concentration of said performic acid is from 1 ppb to 1000 ppm.

47. The method of claim 35 wherein with a one-minute contact time the composition meets or exceeds at least one of the following Standards: BS EN 1276:1997, BS EN 1650:1998, BS EN 13697:2001, BS EN 1276:2009.

48. The method of claim 47, wherein the composition achieves a 100000-fold (5 log) reduction in the cfu of a pathogen grown on a designed growth medium within one minute at 20° C. under dirty conditions of 3.0 g/l bovine albumin, wherein the pathogen is one or more of the reference strains *Listeria monocytogenes* (ATCC 19115), *E. coli* (ATCC 8739), *Staphylococcus aureus* (ATCC 6538), *Pseudomonas aeruginosa* (ATCC 9027) and *Enterococcus hirae* (ATCC 10541).

49. The method of claim 47 wherein the composition exceeds at least one of (a) Standard BS EN 1650:1998 and (b) BS EN 13697:2001.

50. method of claim 49, wherein the composition possesses fungicidal activity within one minute at 20° C. under dirty conditions of 3.0 g/l bovine albumin for one or more of the reference strains *Candida albicans, Aspergillus brasiliensis (Aspergillus niger)*, and *Penecilium* w.t.

51. The method of claim 35 wherein the carboxylic acid contains from 2 to 7 carbon atoms.

52. The method of claim 51 wherein the carboxylic acid is selected from the group consisting of citric acid, propionic acid, lactic acid, salicylic acid, benzoic acid, glyceric acid, oxalic acid, tartaric acid, acetic acid, chloroacetic acid, dichloroacetic acid, trichloroacetic acid, and trifluoroacetic acid, and mixtures thereof.

53. The method of claim 52 wherein the carboxylic acid is selected from the group consisting of citric acid, lactic acid, propionic acid and mixtures thereof.

54. The method of claim 35 wherein said composition contains phosphonic acid, a salt thereof, or a mixture of phosphonic acid and a salt thereof in a concentration of 0.5 to 98 wt. %.

55. The method according to claim 35 wherein said surfactant is an alkyl polyglycoside.

56. The method according to claim 35 wherein said performic acid source is selected from the group consisting of formic acid, formic acid esters, and formic acid salts.

57. The method according to claim 35 wherein said phosphoric acid is present in a concentration of 0.00001 to 98 wt. %.

58. The method according to claim 35 wherein said oxidizer is selected from the group consisting of inorganic peroxides, nitrates, halogens and halogen compounds, hypohalite compounds, ozone, oxides, permanganate salts, multivalent chromium compounds, acids, sulfides and Tollens' reagent.

59. The method according to claim 35 wherein the oxidizer is selected from the group consisting of hydrogen peroxide, sodium percarbonate, sodium periodate, sodium persulfate, ammonium persulfate, sodium perborate, sodium peroxide, calcium peroxide, silver (II) oxide, chlorine dioxide, diacyl peroxides, ketone peroxides, peroxydicarbonates, peroxyesters, dialkyl peroxides, hydroperoxides, peroxyketals, urea hydrogen peroxide, ammonium hydrogen peroxide, ozone, sodium peroxydisulfate, potassium peroxydisulfate and ammonium peroxydisulfate.

60. The method according to claim 35 wherein the concentration of performic acid in said composition decreases by not more than 1% over 6 months at a temperature at or below 20° C.

61. The method according to claim 60 wherein the concentration of performic acid in said composition decreases by not more than 1% over 6 months at a temperature of 20° C.

62. The method of claim 35, wherein, if hydrogen peroxide is present in the composition, the ratio of performic acid to hydrogen peroxide is less than 4:1.

63. The method of claim 47 wherein the composition exceeds at least one of Standard BS EN 1276:1997 and BS EN 1276:2009.

64. The method of claim 63 wherein the composition possesses bactericidal activity within one minute at 20° C. under dirty conditions of 3.0 g/l bovine albumin for the reference strains *E. coli* (ATCC 87391, *Staphylococcus aureus* (ATCC 6538), *Pseudomonas aeruginosa* (ATCC 9027) and *Enterococcus hirae* (ATCC 10541).

65. The method of claim 47 wherein the composition has bactericidal activity against gram-positive bacteria.

66. The method of claim 47 wherein the composition has bactericidal activity against gram-negative bacteria.

67. The method of claim 35, wherein the mass of performic acid (PFA) which is contacted with said fruit or vegetable is not more than 0.0001 times the mass of the fruit or vegetable.

68. The method of claim 35, wherein the ratio of the mass of the PFA which is contacted with said fruit or vegetable to the volume of said fruit or vegetable is not more than 1 g per 0.1 m$^3$.

69. The method of claim 35 wherein the concentration of said performic acid is from 1 ppb to 1000 ppm.

* * * * *